(12) United States Patent
Kim et al.

(10) Patent No.: US 12,048,296 B2
(45) Date of Patent: Jul. 30, 2024

(54) TRANSGENIC MOUSE FOR AGLYCOSYLATED ANTIBODY PRODUCTION AND USE OF AGLYCOSYLATED ANTIBODY PRODUCED THEREFROM

(71) Applicant: KOREA RESEARCH INSTITUTE OF BIOSCIENCE AND BIOTECHNOLOGY, Daejeon (KR)

(72) Inventors: Yong Sam Kim, Daejeon (KR); Jeong Heon Ko, Daejeon (KR); Nan Ee Lee, Daejeon (KR); Sun Hee Kim, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 905 days.

(21) Appl. No.: 16/972,803

(22) PCT Filed: Jun. 7, 2019

(86) PCT No.: PCT/KR2019/006912
§ 371 (c)(1),
(2) Date: Dec. 7, 2020

(87) PCT Pub. No.: WO2019/235895
PCT Pub. Date: Dec. 12, 2019

(65) Prior Publication Data
US 2021/0127649 A1 May 6, 2021

(30) Foreign Application Priority Data
Jun. 7, 2018 (KR) .......... 10-2018-0065394

(51) Int. Cl.
*A01K 67/0276* (2024.01)
*C07K 16/00* (2006.01)
*C12N 9/22* (2006.01)
*C12N 15/11* (2006.01)
*G01N 33/68* (2006.01)

(52) U.S. Cl.
CPC .......... *A01K 67/0276* (2013.01); *C07K 16/00* (2013.01); *C12N 9/22* (2013.01); *C12N 15/11* (2013.01); *G01N 33/68* (2013.01); *A01K 2217/075* (2013.01); *A01K 2227/105* (2013.01); *A01K 2267/01* (2013.01); *C07K 2317/41* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 4,208,479 A * | 6/1980 | Zuk ...................... C07J 41/0016 436/826 |
| 2006/0188439 A1* | 8/2006 | Strome ............. A61K 51/1096 424/1.49 |
| 2010/0015142 A1* | 1/2010 | Koenig .................... A61P 3/10 424/133.1 |

FOREIGN PATENT DOCUMENTS

| CN | 1894406 | 1/2007 |
| CN | 101022828 | 8/2007 |
| CN | 101883500 | 11/2010 |
| CN | 106455512 | 2/2017 |
| CN | 108513582 | 9/2018 |
| EP | 2455758 | 5/2012 |
| JP | 2015-504060 | 2/2015 |
| WO | 9837174 | 8/1998 |
| WO | 2009079242 | 6/2009 |
| WO | 2009134389 | 11/2009 |
| WO | 2011116387 | 9/2011 |

OTHER PUBLICATIONS

Jung (ACS Chem. Biol. 2013 8:368-375) (Year: 2013).*
Jo (MABS Feb. 2018 10:278-289) (Year: 2018).*
Zhao Xiao-Fan, "Basis scientific questions and molecular biology techniques in entomology", Acta Entomologica Sinica, Aug. 2016, 59(8): 896-905.
SIPO, Office Action of CN 201980050543.5 dated Jan. 24, 2022 (English translation only).
Nicole M. Gaudelli et al., "Programmable base editing of A•T to G•C in genomic DNA without DNA cleavage", Nature. Nov. 23, 2017; 551(7681): 464-471. doi:10.1038/nature24644.
Dmitrij Hristodorov et al., "Generation and Comparative Characterization of Glycosylated and Aglycosylated Human IgG1 Antibodies", Mol Biotechnol (2013) 53:326-335. DOI 10.1007/s12033-012-9531-x.
Man-Seok Ju et al., "Aglycosylated full-length IgG antibodies: steps toward next-generation immunotherapeutics", Current Opinion in Biotechnology 2014, 30:128-139. http://dx.doi.org/10.1016/j.copbio.2014.06.013.
Wei Li et al., "Crystallizable Fragment Glycoengineering for Therapeutic Antibodies Development", Front. Immunol. 8:1554, Nov. 2017. doi: 10.3389/fimmu.2017.01554.

(Continued)

*Primary Examiner* — Changhwa J Cheu
(74) *Attorney, Agent, or Firm* — LEX IP MEISTER, PLLC

(57) ABSTRACT

The present disclosure relates to an aglycosylated antibody-producing transgenic mouse and the use of an aglycosylated antibody produced therefrom. When the transgenic mouse of the present disclosure is used, it is possible to easily produce aglycosylated antibodies against various target antigens, and to precisely diagnose disease by detecting a glycoprotein biomarker using the produced aglycosylated antibody.

8 Claims, 28 Drawing Sheets

Specification includes a Sequence Listing.

(56) References Cited

OTHER PUBLICATIONS

Peiqing Zhang et al., "Challenges of glycosylation analysis and control: an integrated approach to producing optimal and consistent therapeutic drugs", Drug Discovery Today, vol. 21, Issue 5, May 2016, pp. 740-765. http://dx.doi.org/10.1016/j.drudis.2016.01.006.
Dave Li et al., "AFP-L3: a new generation of tumor marker for hepatocellular carcinoma", Clin Chim Acta. Nov. 2001;313(1-2):15-9. doi: 10.1016/s0009-8981(01)00644-1.
JPO, Office Action of JP 2020-568257 dated Mar. 7, 2022.
Seuk-Min Ryu et al., "Adenine base editing in mouse embryos and an adult mouse model of Duchenne muscular dystrophy", Nat Biotechnol 36, 536-539 (2018), Apr. 27, 2018; https://doi.org/10.1038/nbt.4148.
Meilyn Rodrfguez et al., "Transgenic plants of *Nicoticma tabacum* L. express aglycosylated monoclonal antibody with antitumor activity," Biofecnologia Aplicada 2013; Vo.30, No. 2, 157-161.
Gang Yin et al., "Aglycosylated antibodies and antibody fragments produced in a scalable in vitro transcription-translation system," mAbs, vol. 4, No. 2, pp. 217-225, 2012, doi: https://doi.org/10.4161/mabs.4.2.19202.

\* cited by examiner

[Fig. 1]
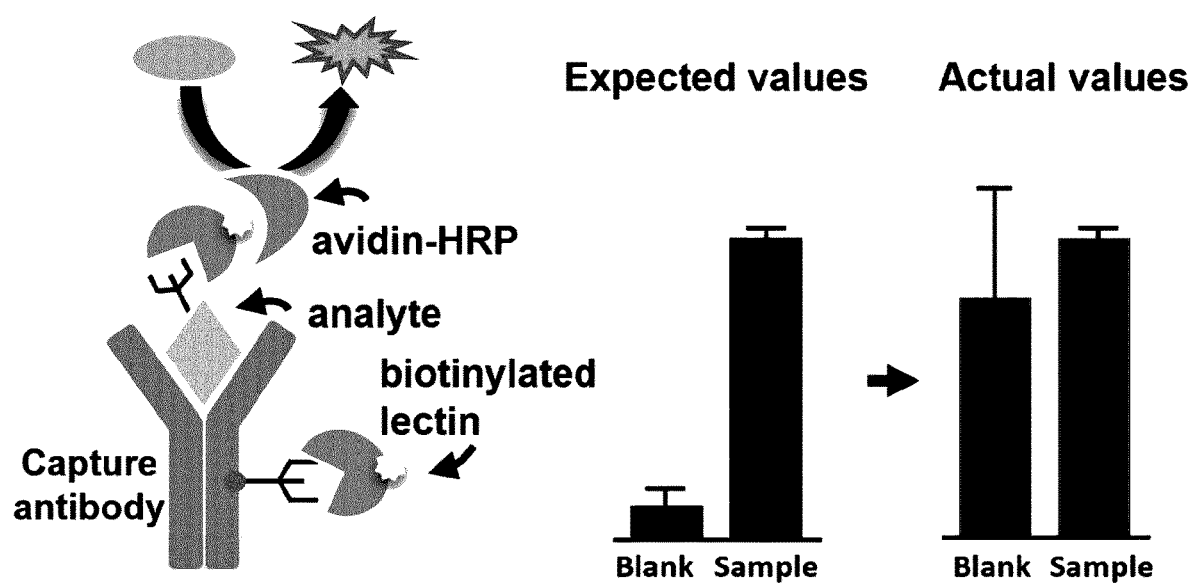

[Fig. 2]
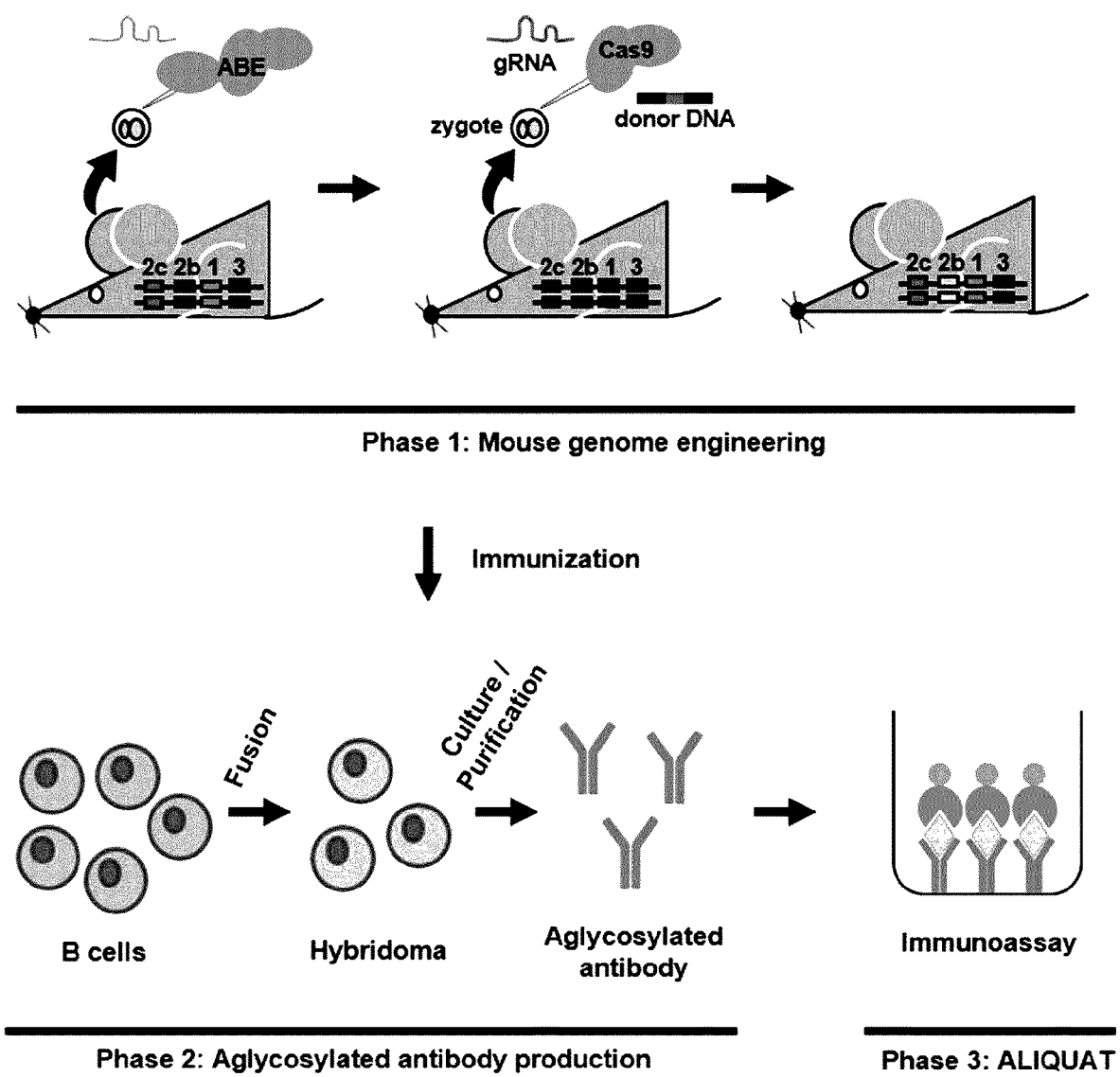

[Fig. 3]
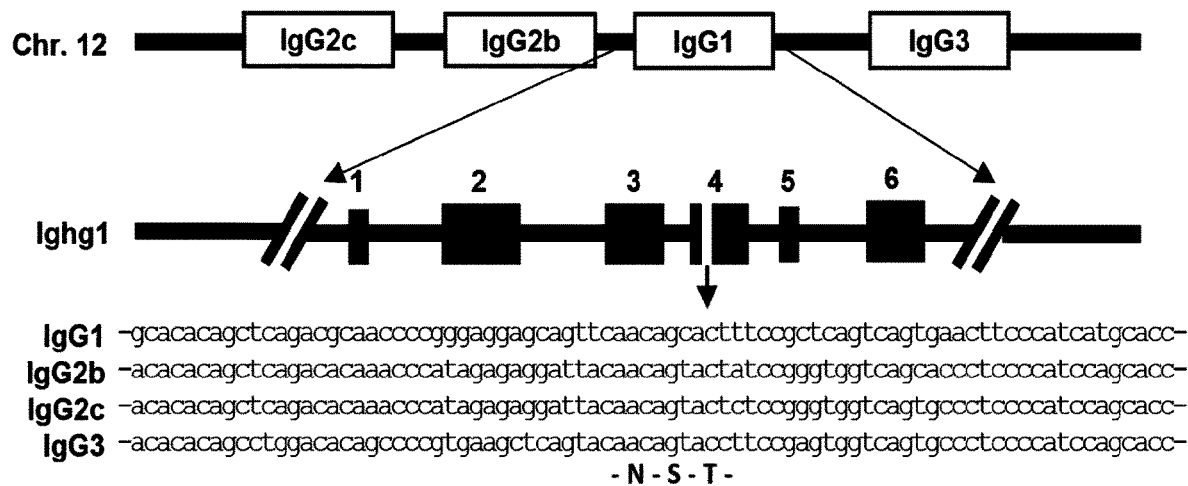

[Fig. 4]
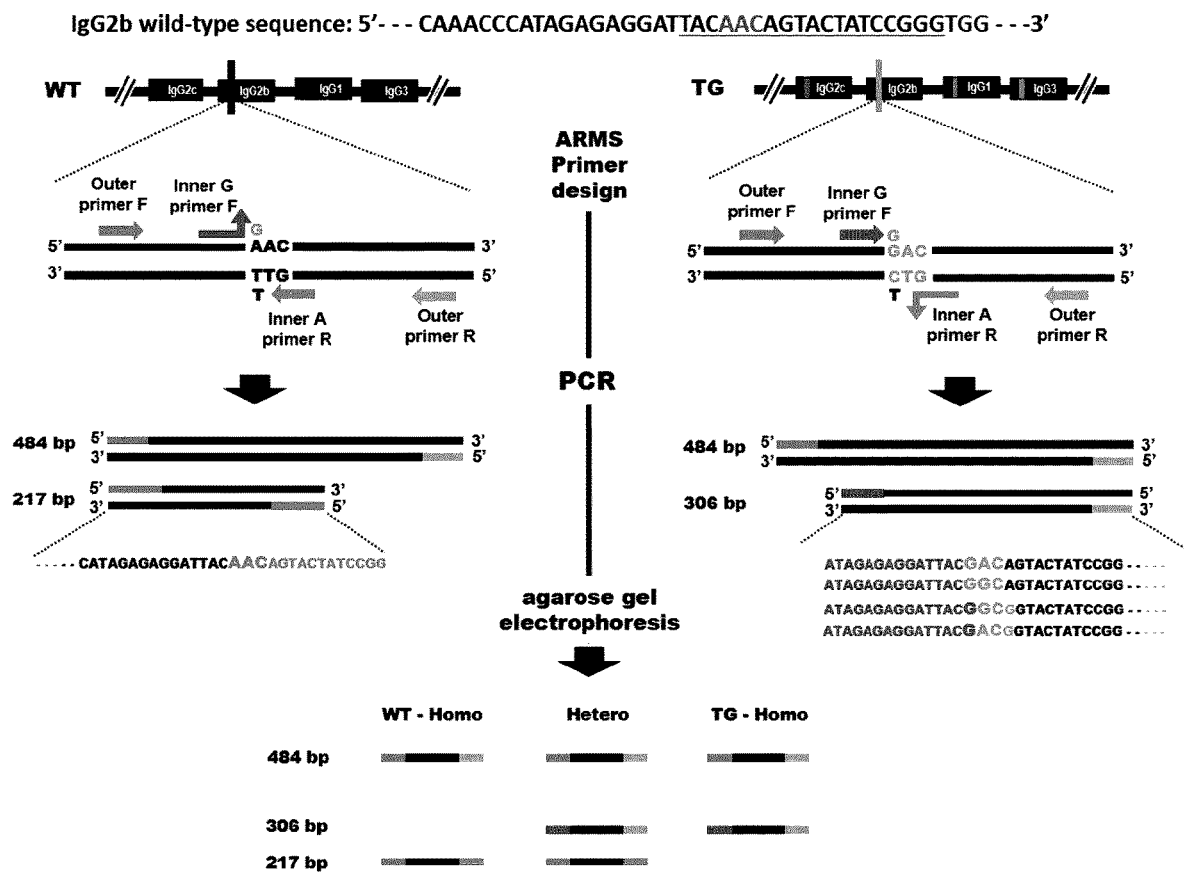

[Fig. 5]
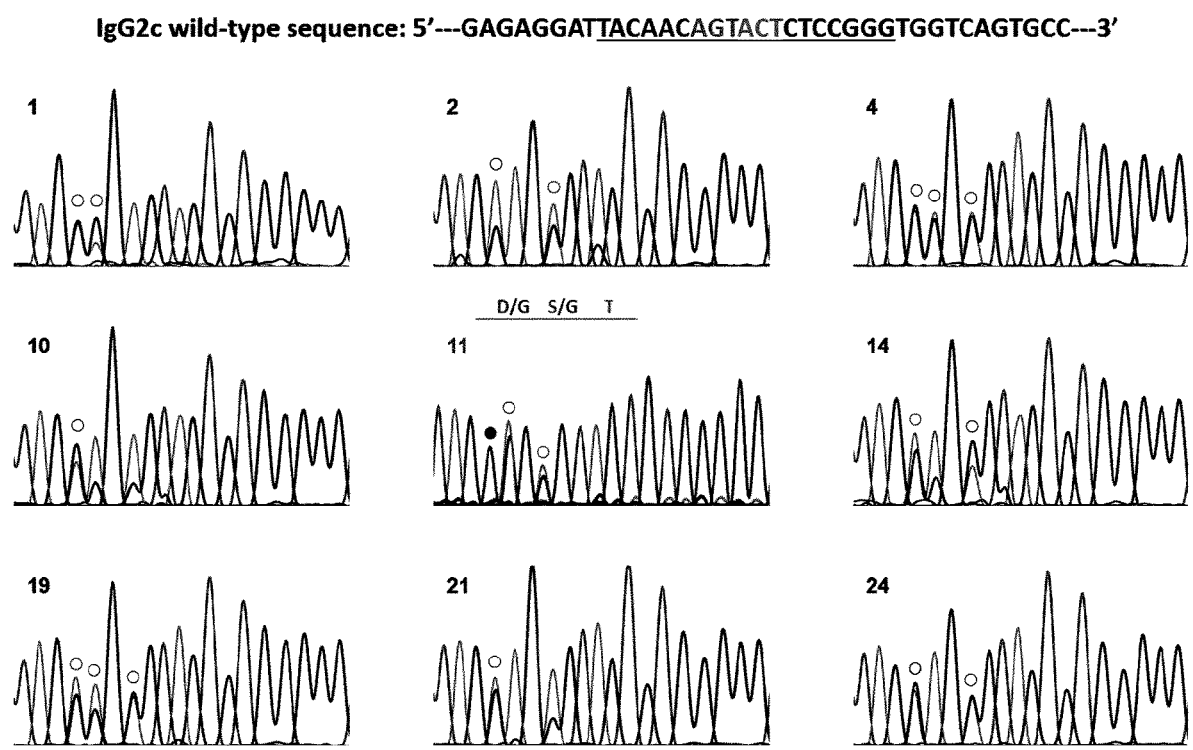

[Fig. 6]
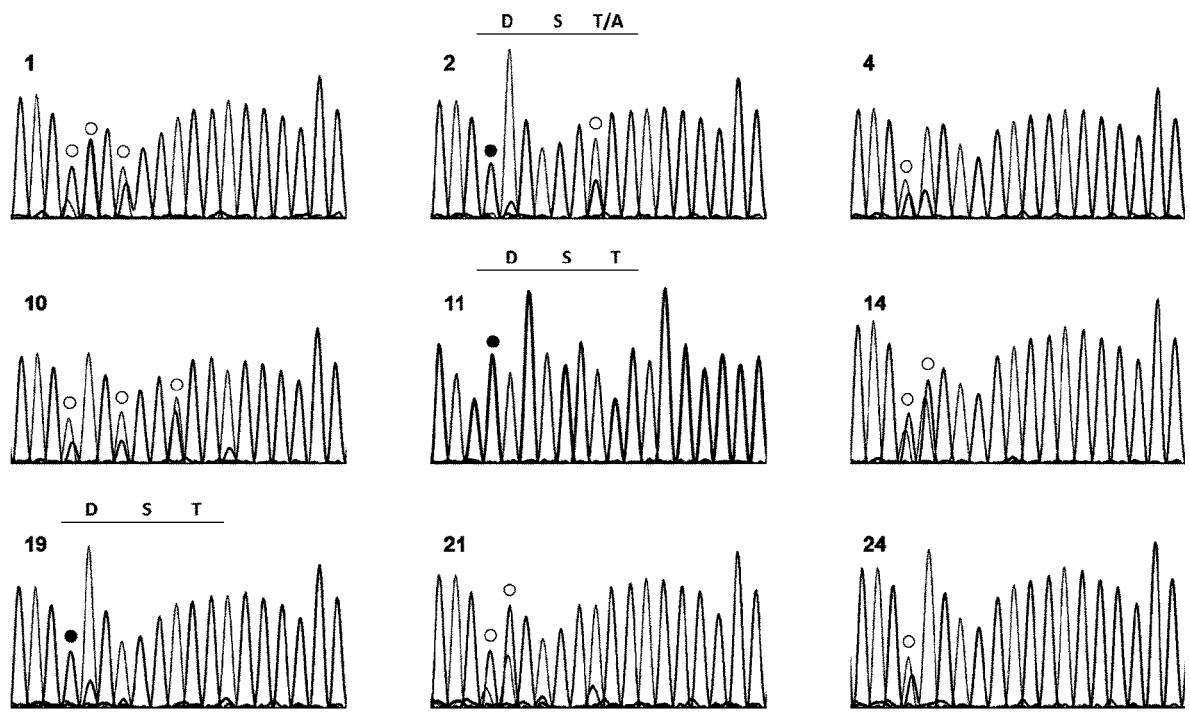

[Fig. 7]
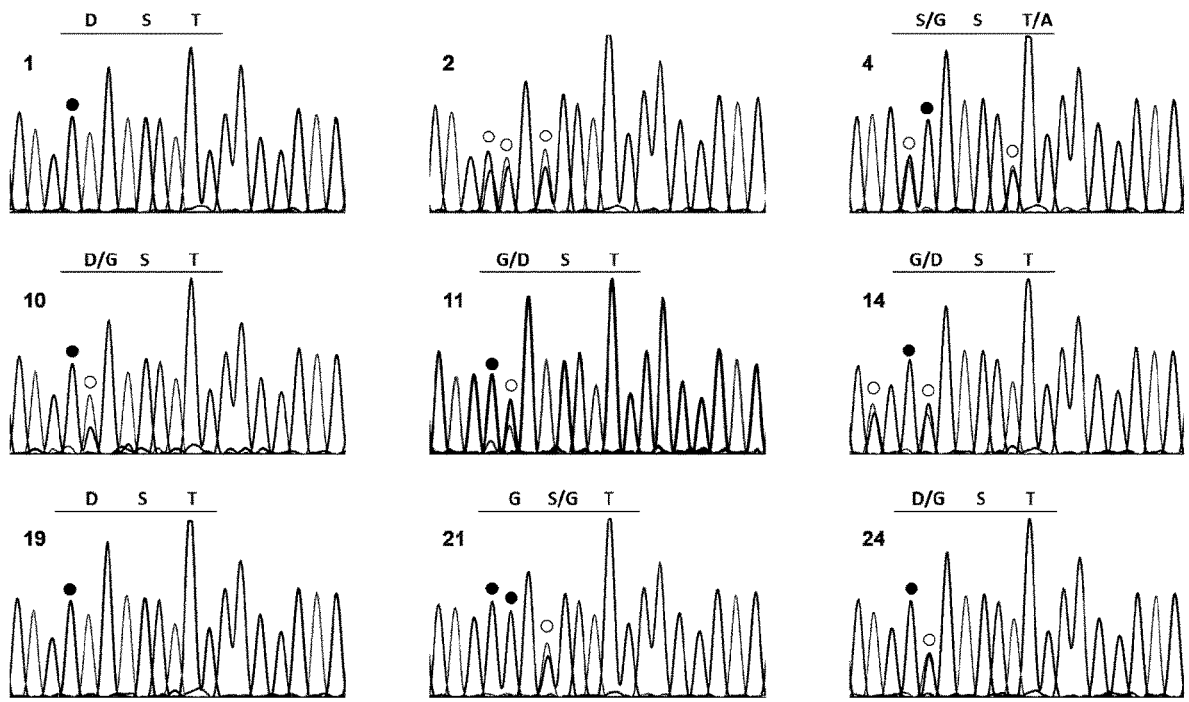

[Fig. 8]
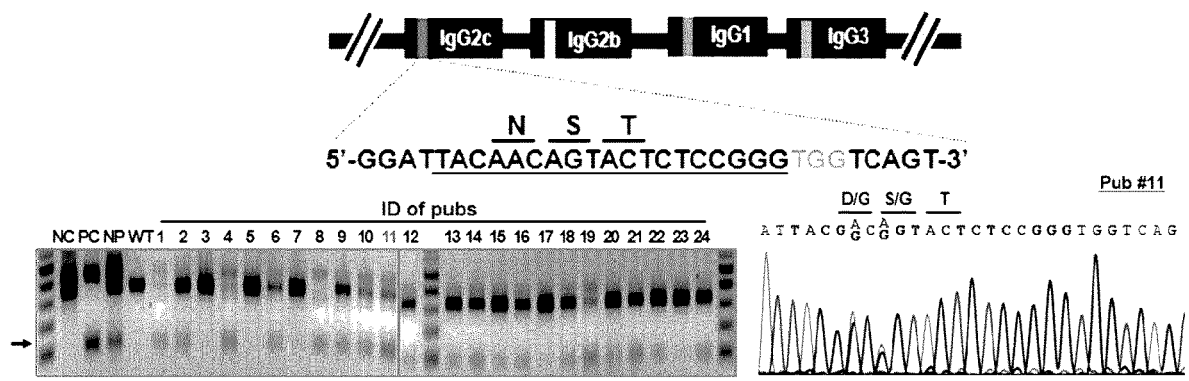

[Fig. 9]
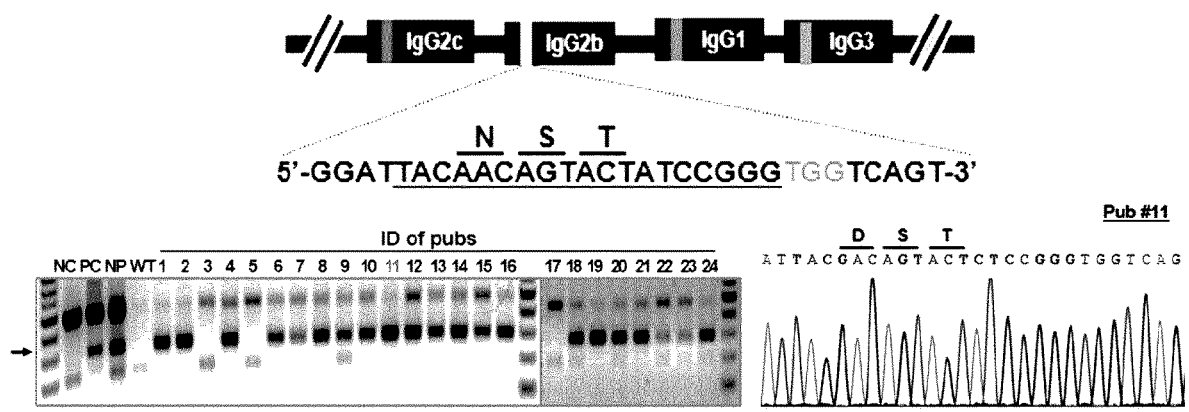
[Fig. 10]
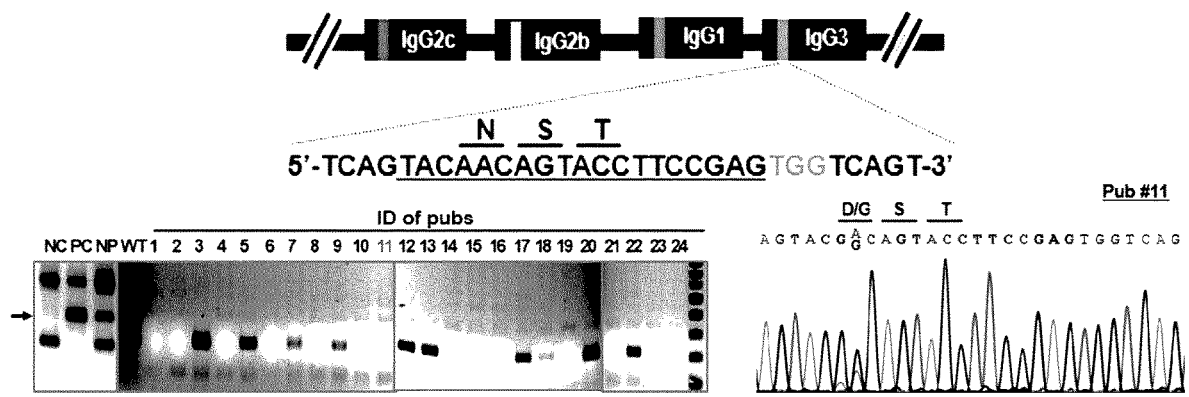

[Fig. 11]
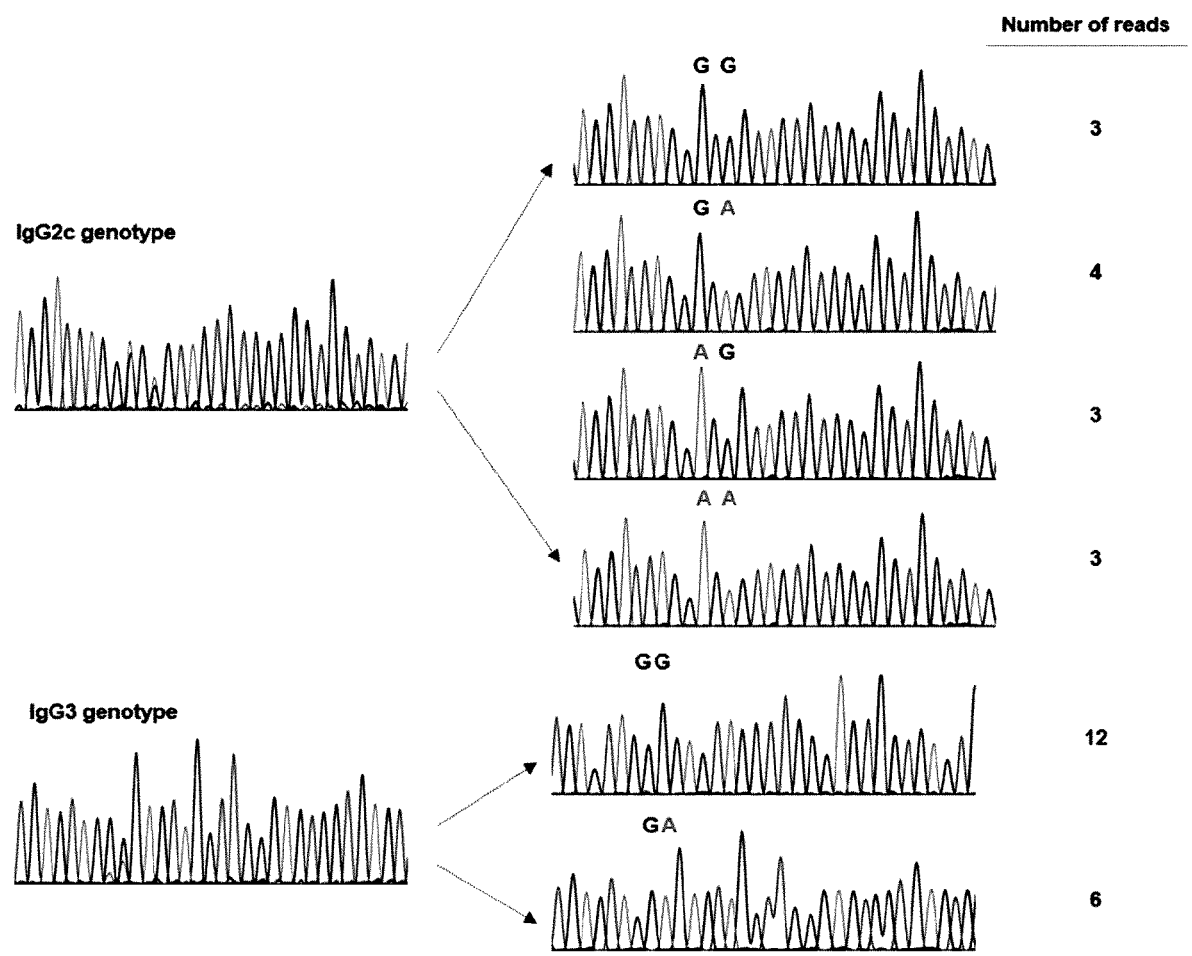

[Fig. 12]
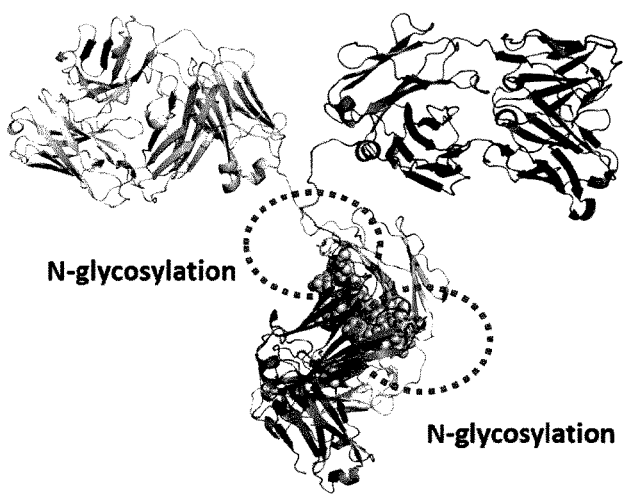
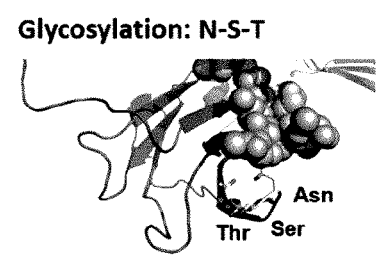
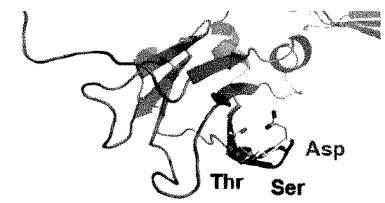
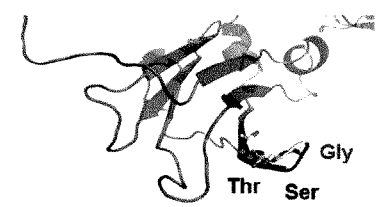

[Fig. 13]
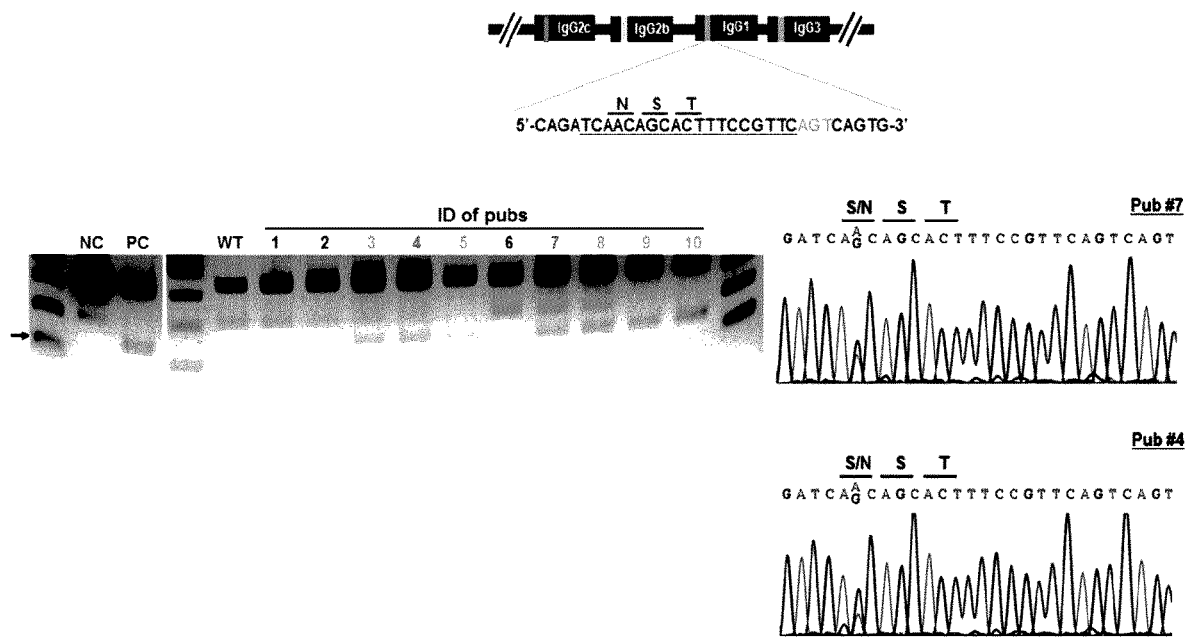

[Fig. 14]
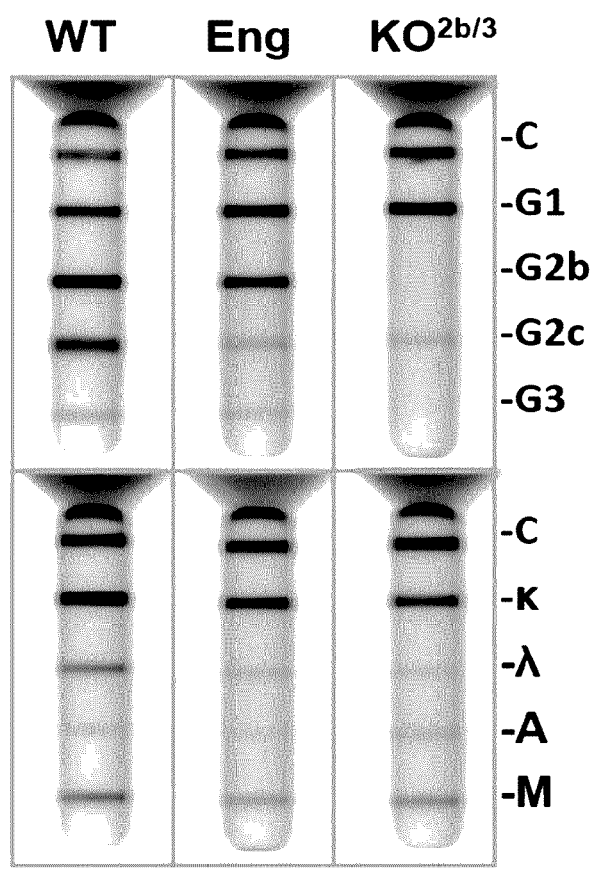

[Fig. 15]
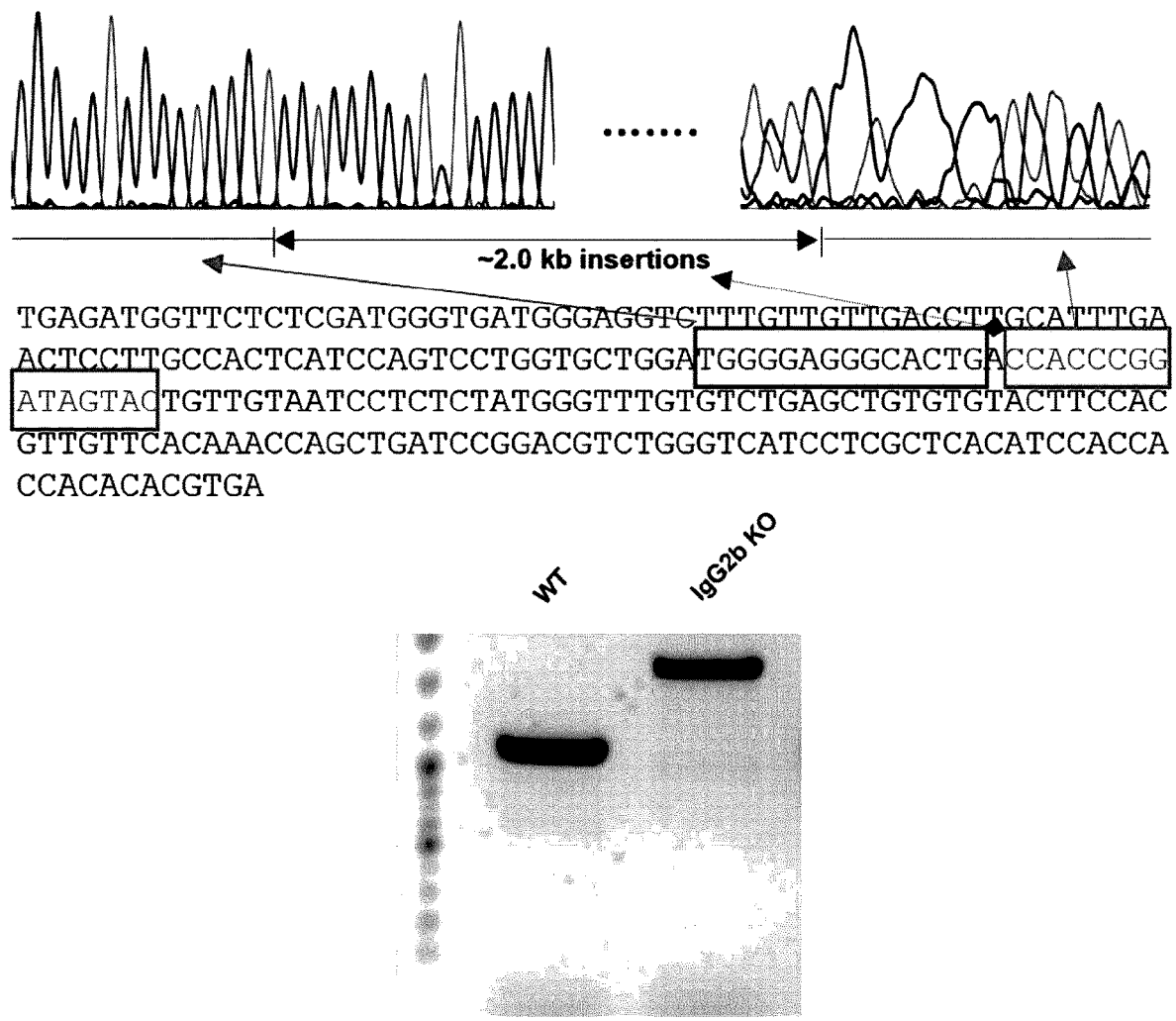

[Fig. 16]

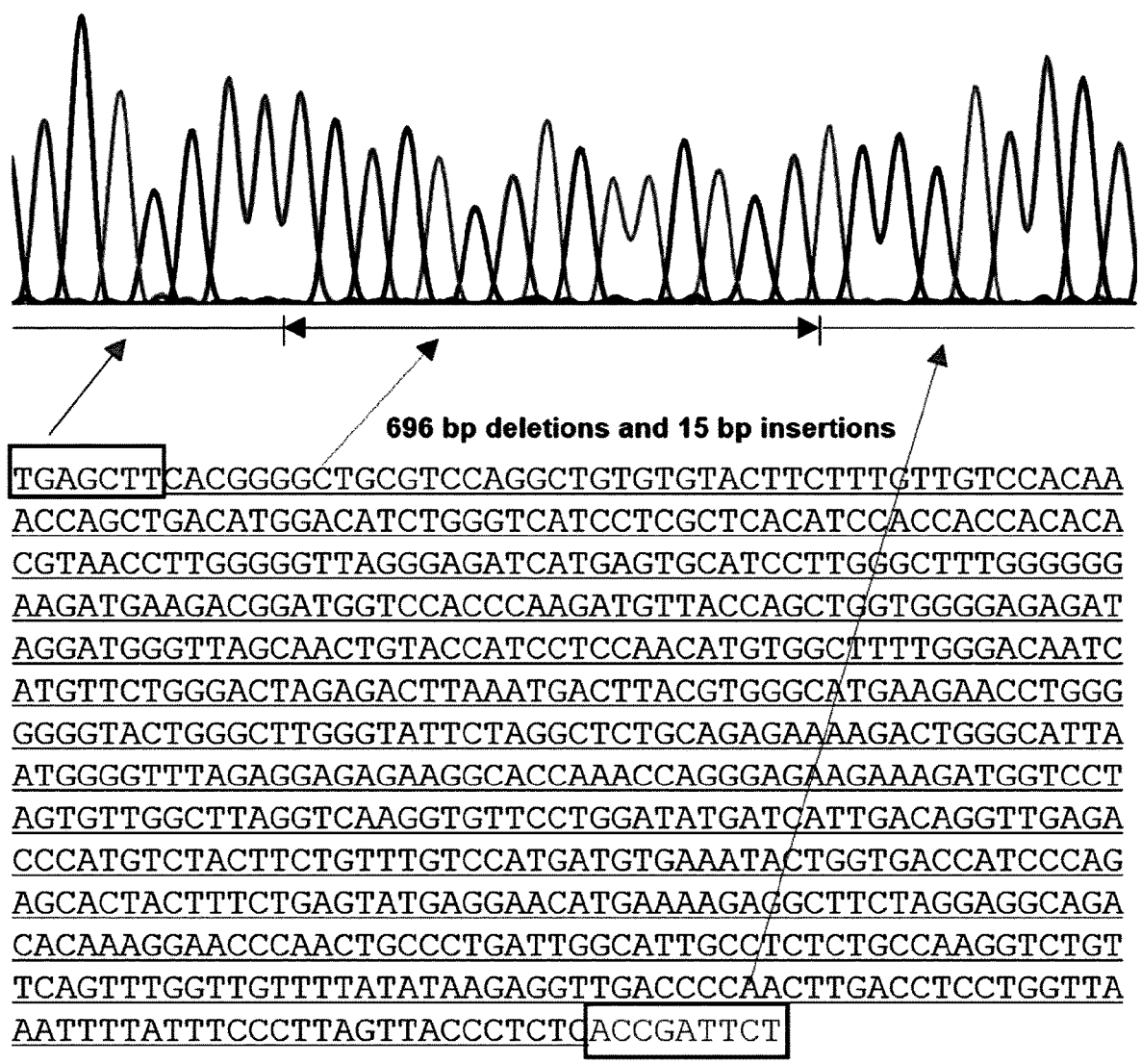

696 bp deletions and 15 bp insertions

TGAGCTTCACGGGGCTGCGTCCAGGCTGTGTGTACTTCTTTGTTGTCCACAA
ACCAGCTGACATGGACATCTGGGTCATCCTCGCTCACATCCACCACCACACA
CGTAACCTTGGGGGTTAGGGAGATCATGAGTGCATCCTTGGGCTTTGGGGGG
AAGATGAAGACGGATGGTCCACCCAAGATGTTACCAGCTGGTGGGGAGAGAT
AGGATGGGTTAGCAACTGTACCATCCTCCAACATGTGGCTTTTGGGACAATC
ATGTTCTGGGACTAGAGACTTAAATGACTTACGTGGGCATGAAGAACCTGGG
GGGGTACTGGGCTTGGGTATTCTAGGCTCTGCAGAGAAAGACTGGGCATTA
ATGGGGTTTAGAGGAGAGAAGGCACCAAACCAGGGAGAAGAAAGATGGTCCT
AGTGTTGGCTTAGGTCAAGGTGTTCCTGGATATGATCATTGACAGGTTGAGA
CCCATGTCTACTTCTGTTTGTCCATGATGTGAAATACTGGTGACCATCCCAG
AGCACTACTTTCTGAGTATGAGGAACATGAAAAGAGGCTTCTAGGAGGCAGA
CACAAAGGAACCCAACTGCCCTGATTGGCATTGCCTCTCTGCCAAGGTCTGT
TCAGTTTGGTTGTTTTATATAAGAGGTTGACCCCAACTTGACCTCCTGGTTA
AATTTTATTTCCCTTAGTTACCCTCTCACCGATTCT

[Fig. 17]
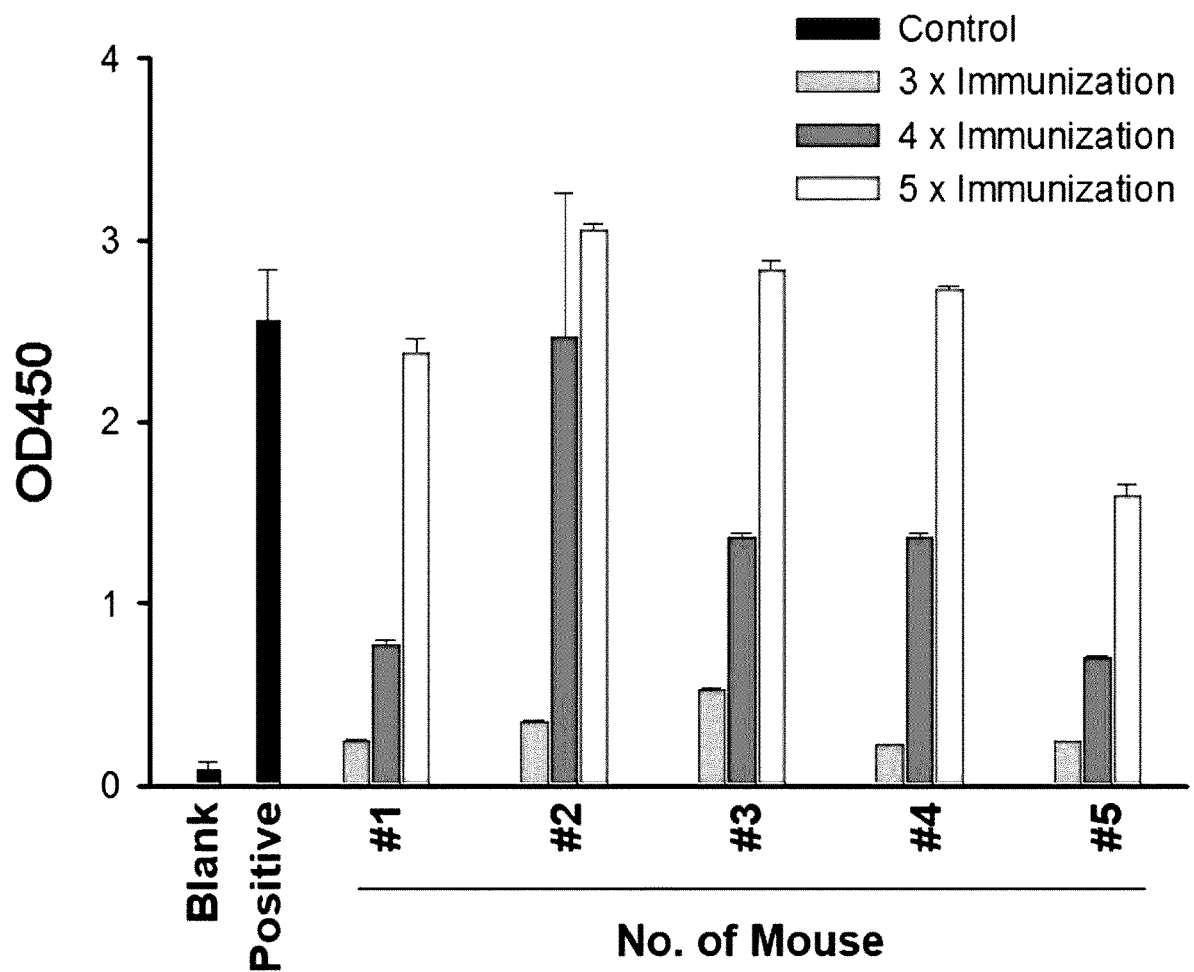

[Fig. 18]
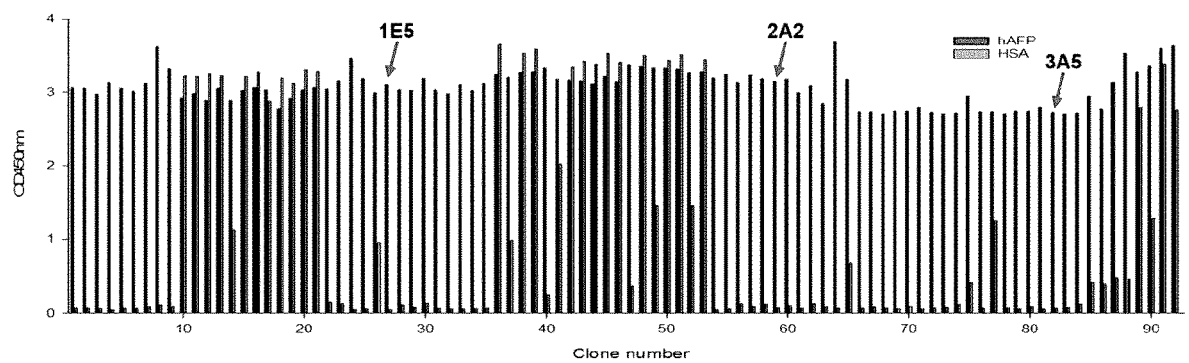
[Fig. 19]
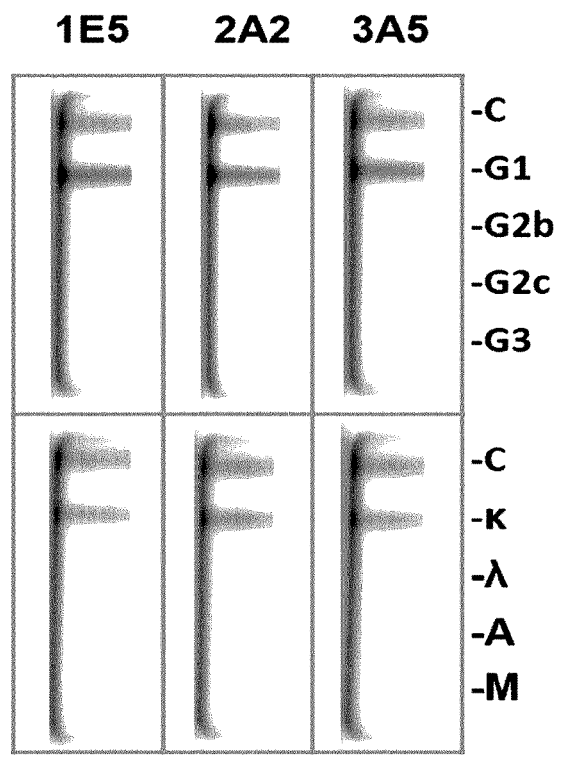

[Fig. 20]
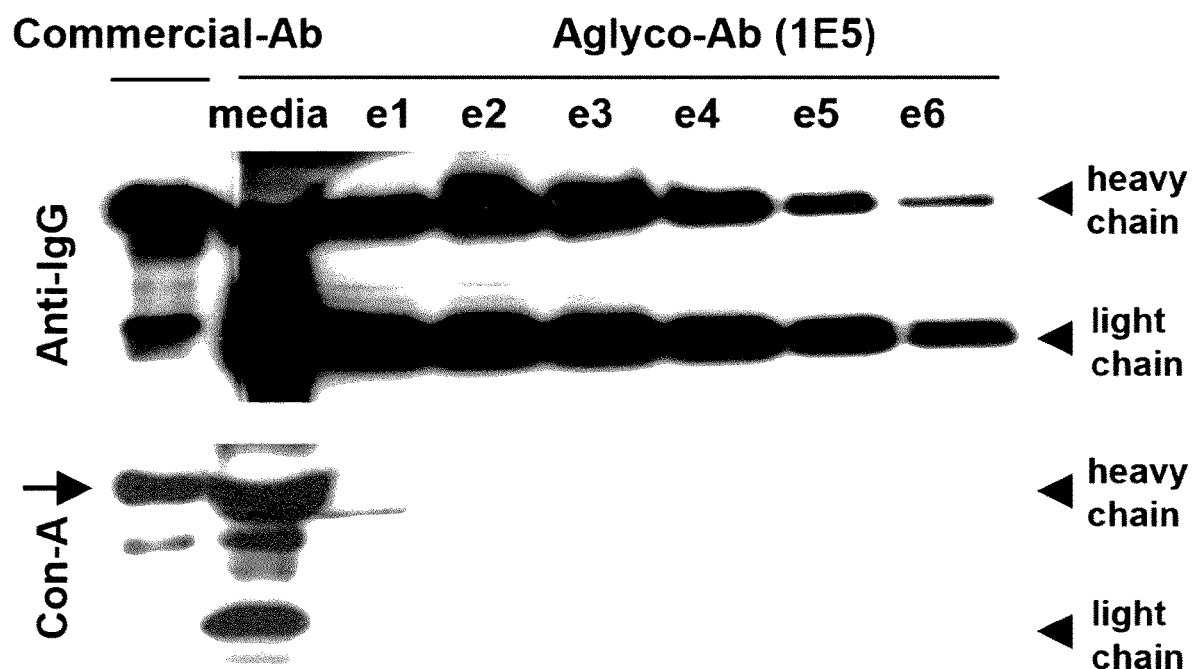

[Fig. 21]
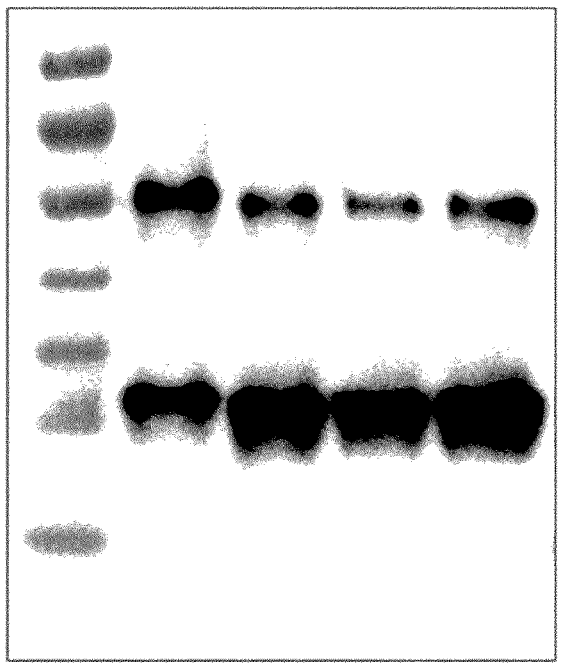
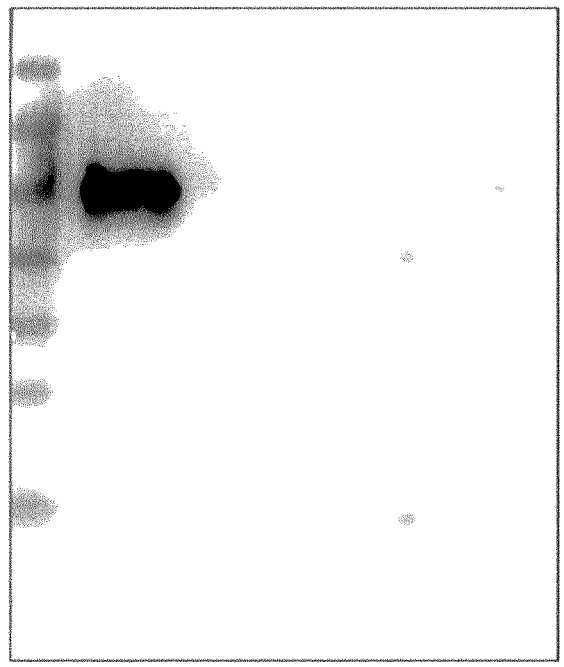
Anti-mouse IgG          Concanavalin-A

[Fig. 22]
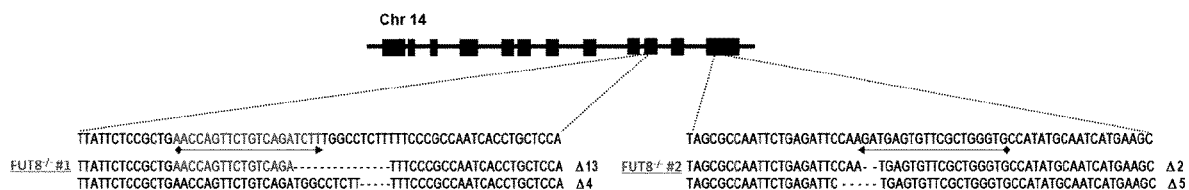

[Fig. 23]
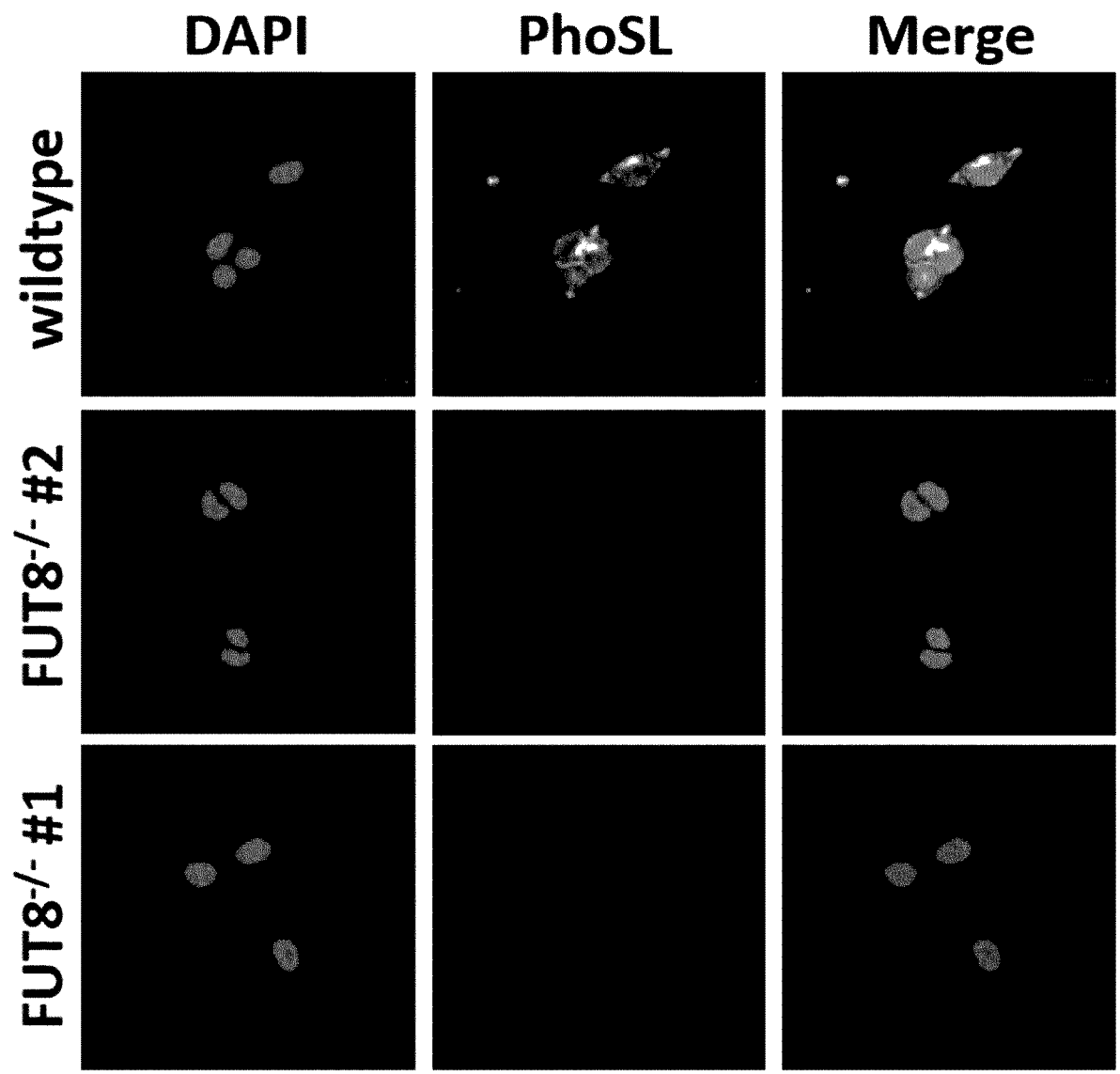

[Fig. 24]
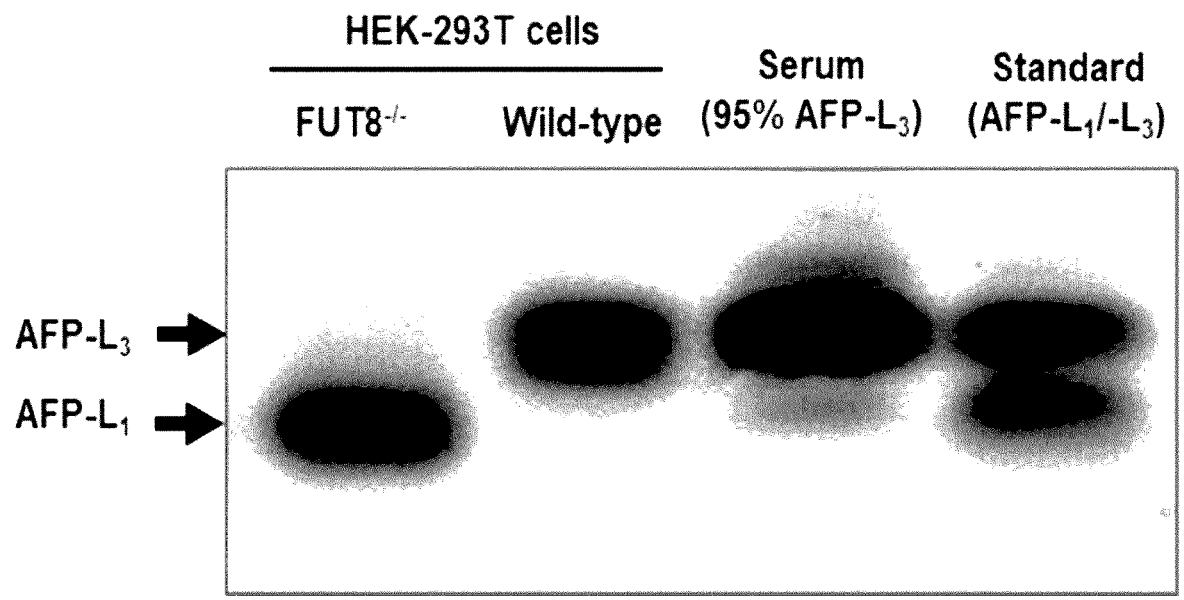
[Fig. 25]
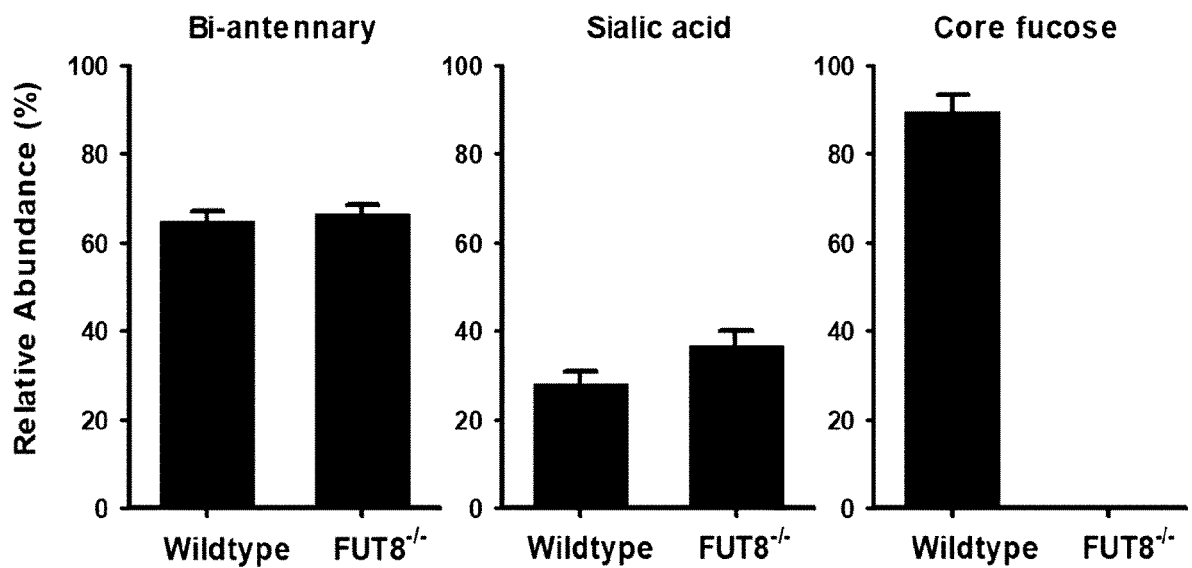

[Fig. 26]
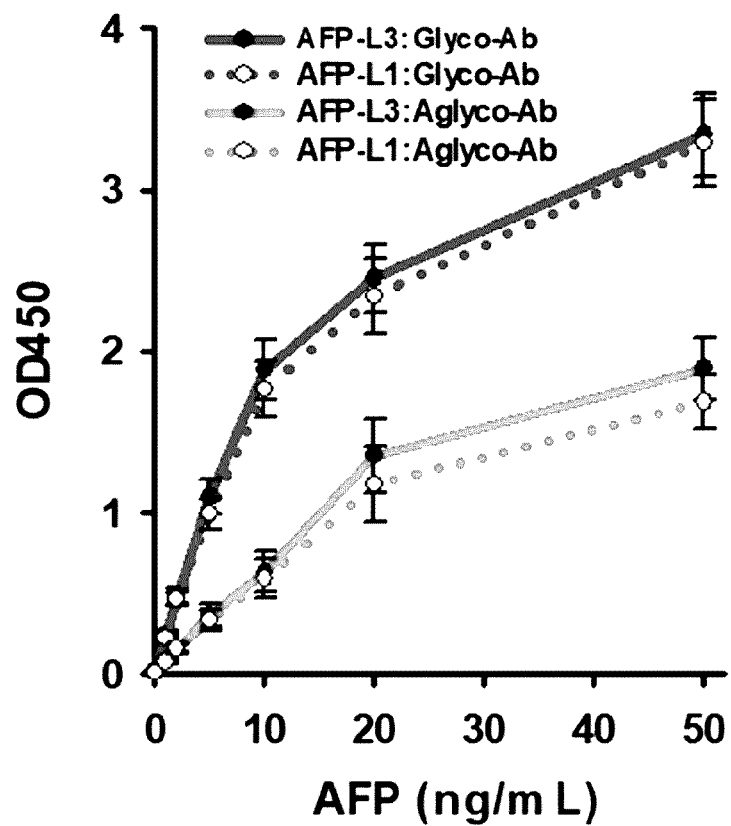

[Fig. 27]
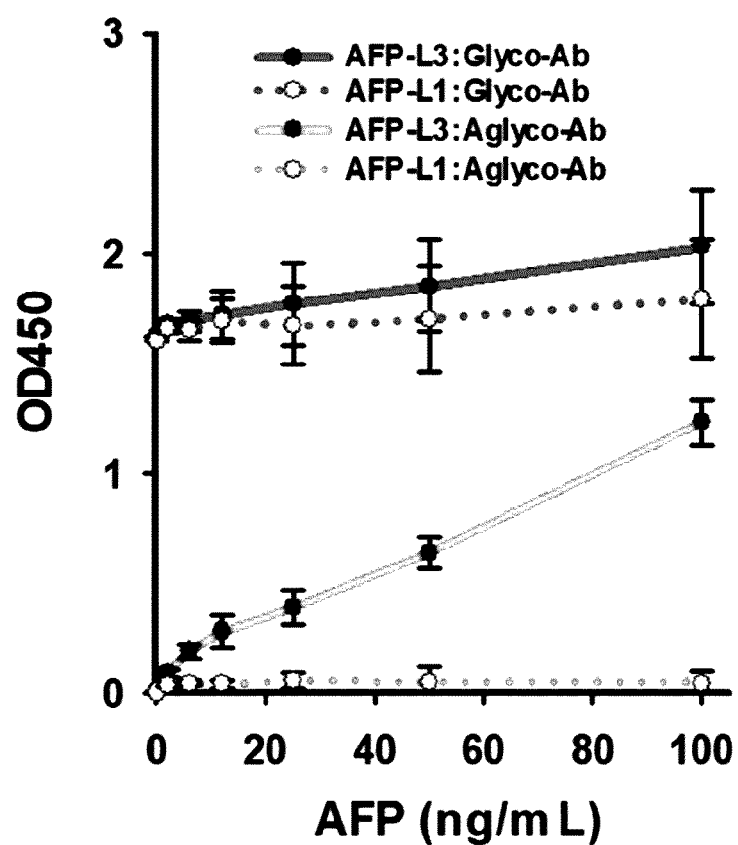

[Fig. 28]
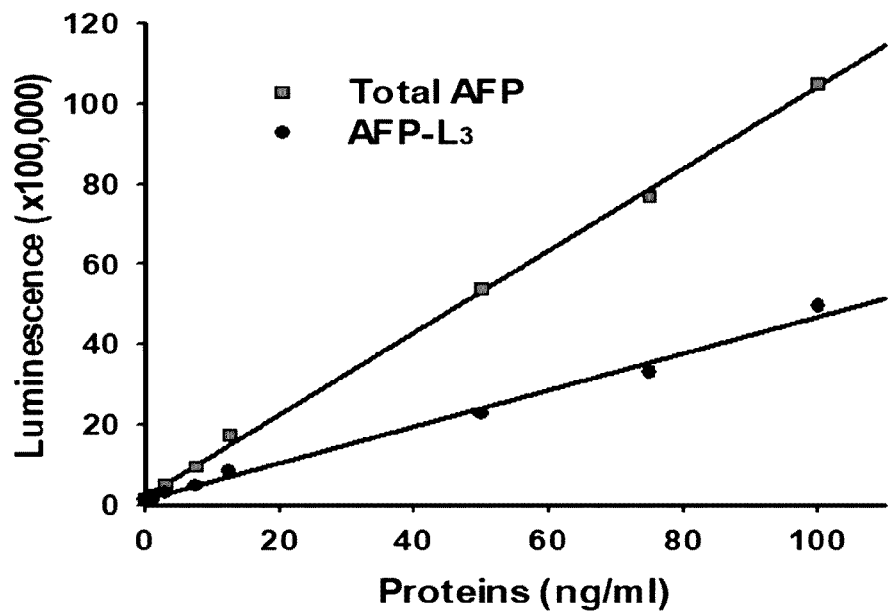
[Fig. 29]
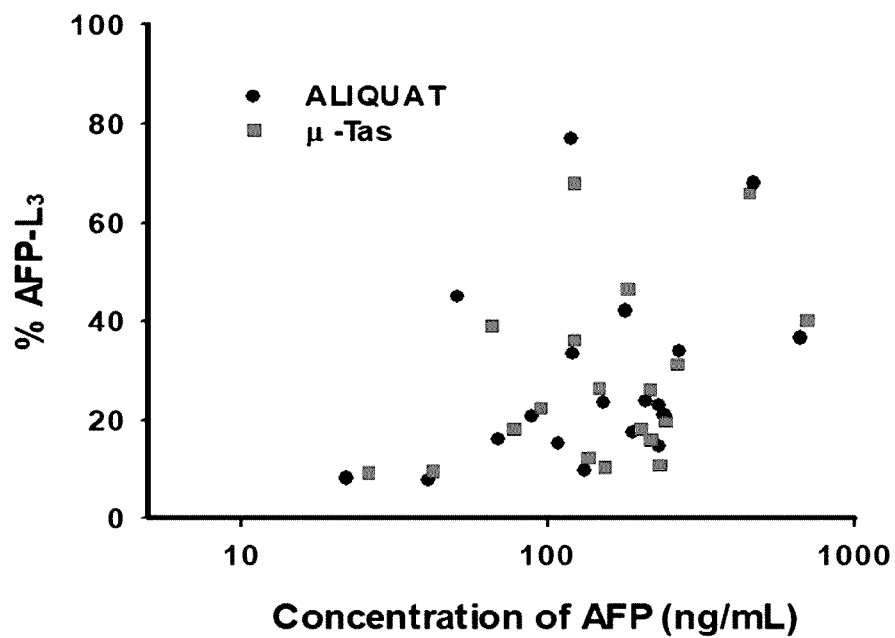

[Fig. 30]
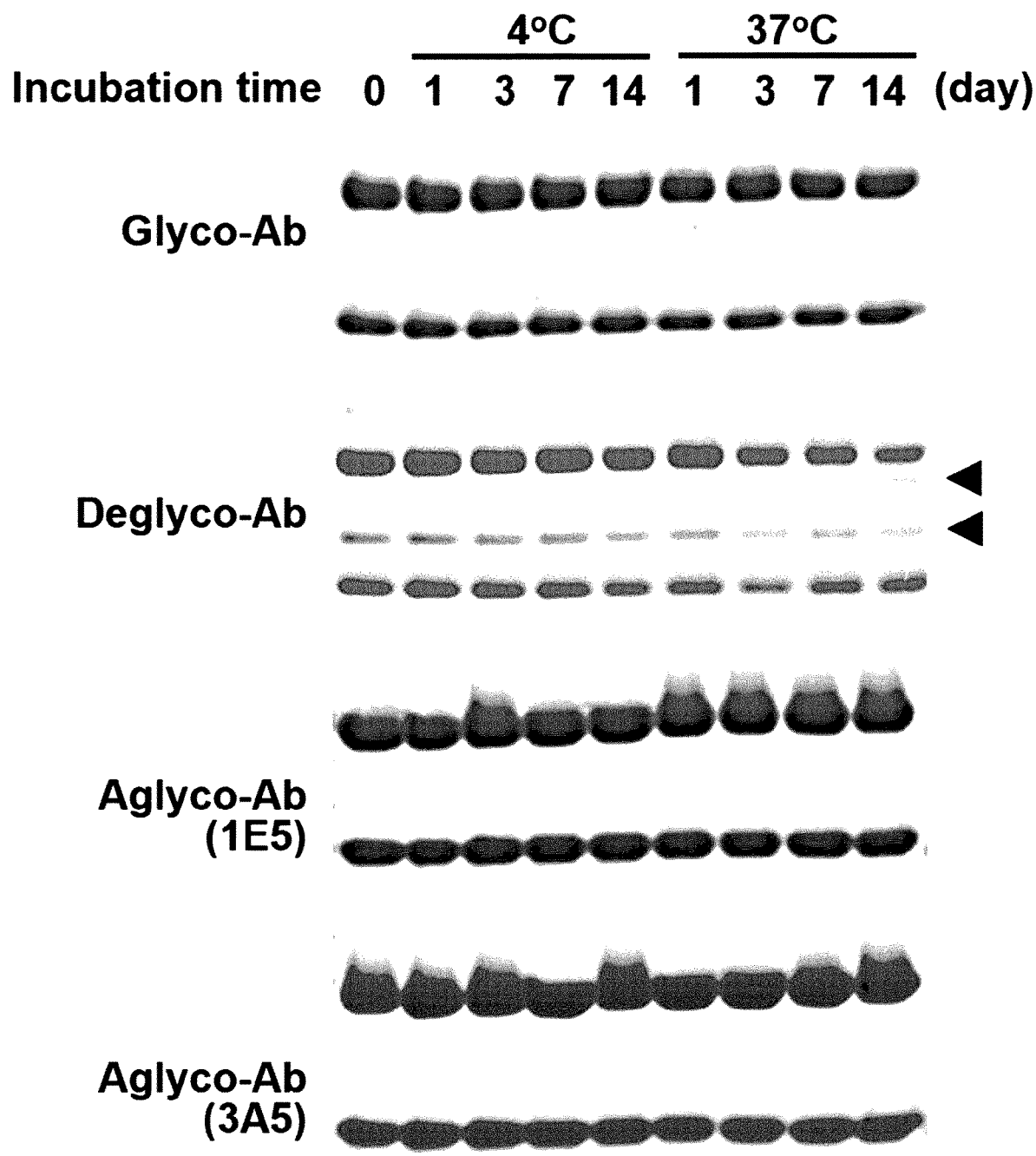

[Fig. 31]
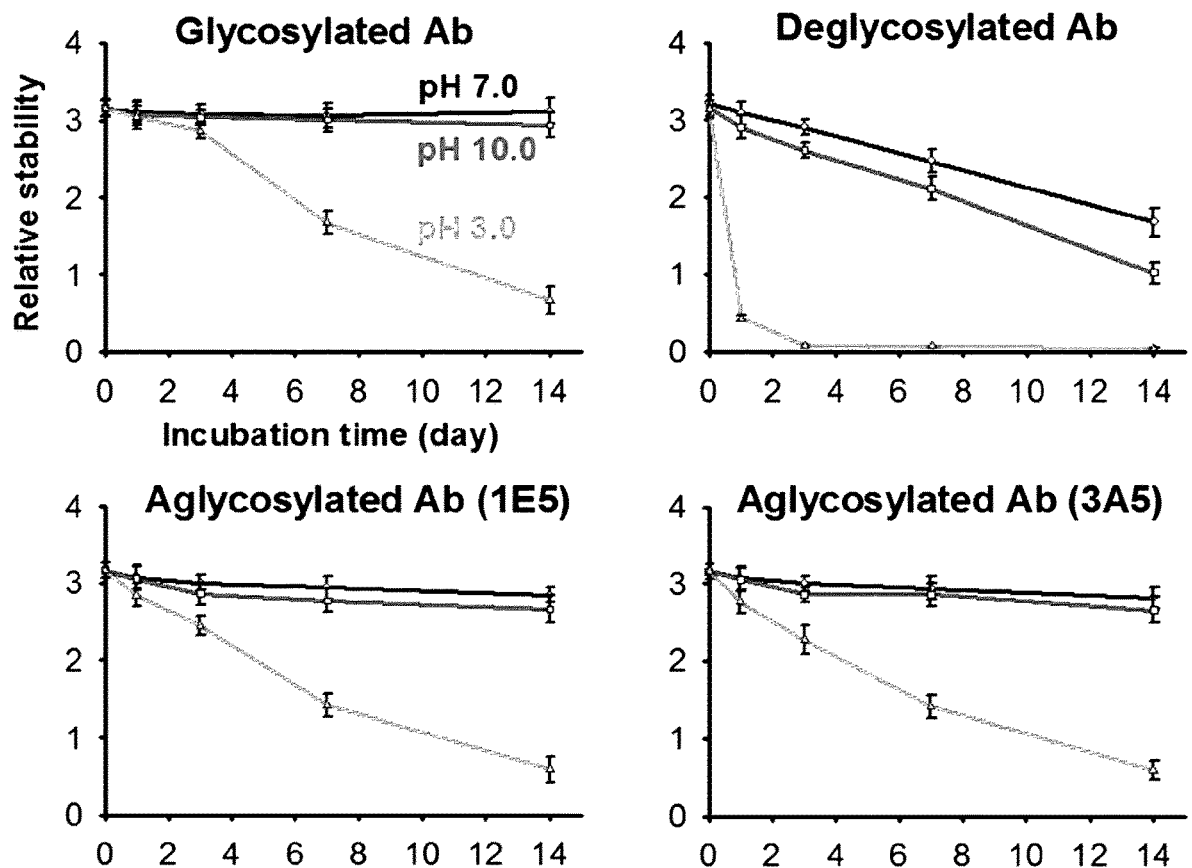

[Fig. 32]
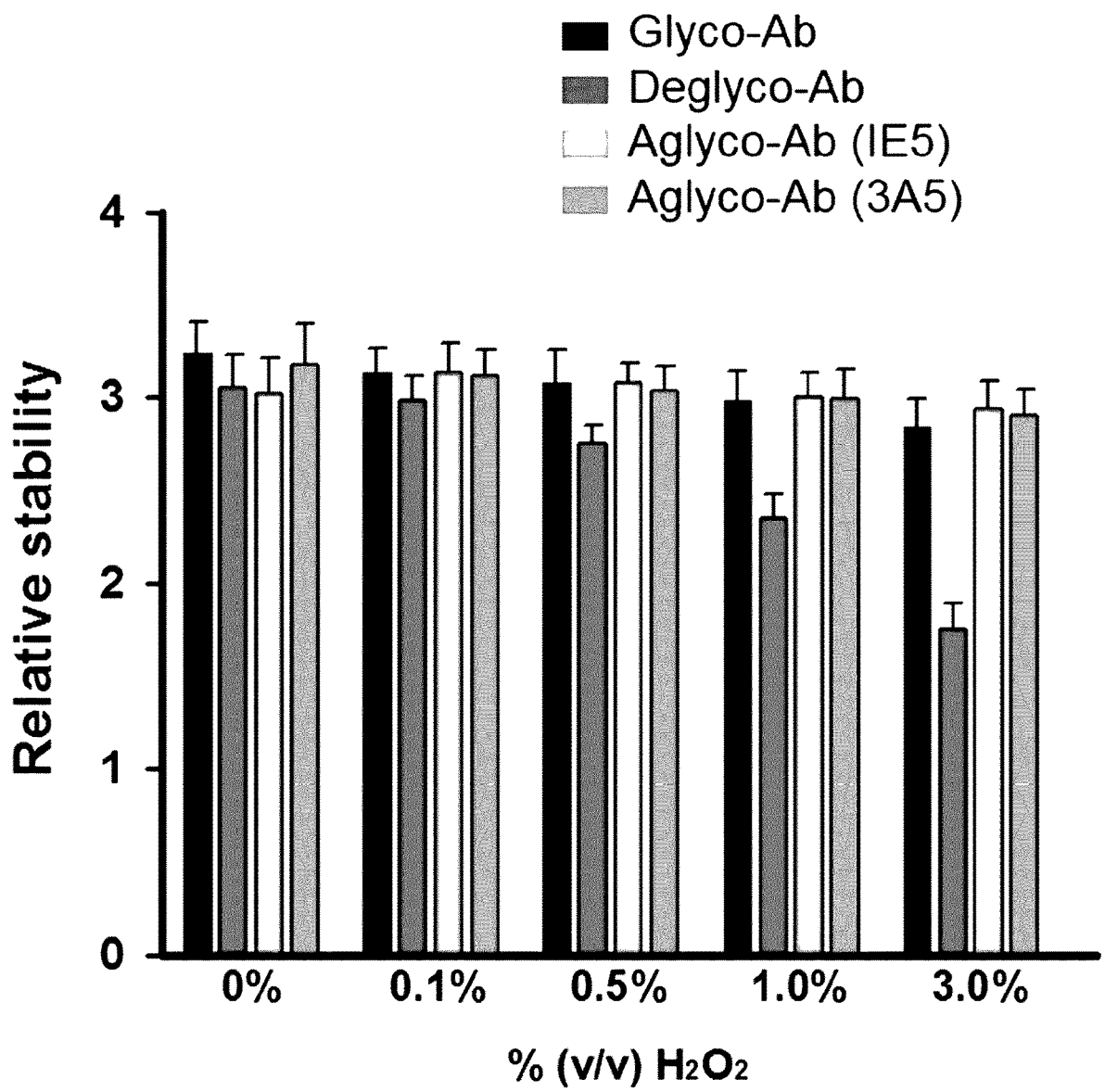

SEQUENCE LISTING

<160> NUMBER OF SEQ ID NOS: 40

<210> SEQ ID NO 1
<211> LENGTH: 5328
<212> TYPE: DNA
<213> ORGANISM: Artificial Sequence
<220> FEATURE:
<223> OTHER INFORMATION: ABE

<400> SEQUENCE: 1

```
atgtccgaag tcgagttttc ccatgagtac tggatgagac acgcattgac tctcgcaaag      60
agggcttggg atgaacgcga ggtgcccgtg ggggcagtac tcgtgcataa caatcgcgta     120
atcggcgaag gttggaatag gccgatcgga cgccacgacc ccactgcaca tgcggaaatc     180
atggcccttc gacagggagg gcttgtgatg cagaattatc gacttatcga tgcgacgctg     240
tacgtcacgc ttgaaccttg cgtaatgtgc gcgggagcta tgattcactc ccgcattgga     300
cgagttgtat tcggtgcccg cgacgccaag acgggtgccg caggttcact gatggacgtg     360
ctgcatcacc caggcatgaa ccaccgggta gaaatcacag aaggcatatt ggcggacgaa     420
tgtgcggcgc tgttgtccga cttttttcgc atgcggaggc aggagatcaa ggcccagaaa     480
aaagcacaat cctctactga ctctggtggt tcttctggtg gttctagcgg cagcgagact     540
cccgggacct cagagtccgc cacacccgaa agttctggtg gttcttctgg tggttcttcc     600
gaagtcgagt tttcccatga gtactggatg agacacgcat tgactctcgc aaagagggct     660
cgagatgaac gcgaggtgcc cgtggggca gtactcgtgc tcaacaatcg cgtaatcggc     720
gaaggttgga atagggcaat cggactccac gaccccactg cacatgcgga aatcatggcc     780
cttcgacagg gagggcttgt gatgcagaat tatcgactta tcgatgcgac gctgtacgtc     840
acgtttgaac cttgcgtaat gtgcgcggga gctatgatta ctcccgcat tggacgagtt     900 gtattcggtg ttcgcaacgc aagacgggt gccgcaggtt cactgatgga cgtgctgcat     960
tacccaggca tgaaccaccg ggtagaaatc acagaaggca tattggcgga cgaatgtgcg    1020
gcgctgttgt gttacttttt tcgcatgccc aggcaggtct taacgccca gaaaaaagca    1080 caatcctcta ctgactctgg tggttcttct ggtggttcta gcggcagcga gactcccggg    1140
acctcagagt ccgccacacc cgaaagttct ggtggttctt ctggtggttc tgataaaaag    1200
tattctattg gtttagccat cggcactaat tccgttggat gggctgtcat aaccgatgaa    1260
```

```
tacaaagtac cttcaaagaa atttaaggtg ttggggaaca cagaccgtca ttcgattaaa      1320
aagaatctta tcggtgccct cctattcgat agtggcgaaa cggcagaggc gactcgcctg      1380
aaacgaaccg ctcggagaag gtatacacgt cgcaagaacc gaatatgtta cttacaagaa      1440
atttttagca atgagatggc caaagttgac gattctttct ttcaccgttt ggaagagtcc      1500
ttccttgtcg aagaggacaa gaaacatgaa cggcacccca tctttggaaa catagtagat      1560
gaggtggcat atcatgaaaa gtacccaacg atttatcacc tcagaaaaaa gctagttgac      1620
tcaactgata aagcggacct gaggttaatc tacttggctc ttgcccatat gataaagttc      1680
cgtgggcact ttctcattga gggtgatcta aatccggaca actcggatgt cgacaaactg      1740
ttcatccagt tagtacaaac ctataatcag ttgtttgaag agaaccctat aaatgcaagt      1800
ggcgtggatg cgaaggctat tcttagcgcc cgcctctcta atcccgacg gctagaaaac       1860 ctgatcgcac aattacccgg agagaagaaa atgggttgt tcggtaaccct tatagcgctc      1920 tcactaggcc tgacaccaaa ttttaagtcg aacttcgact tagctgaaga tgccaaattg      1980
cagcttagta aggacacgta cgatgacgat ctcgacaatc tactggcaca aattggagat      2040
cagtatgcgg acttattttt ggctgccaaa aaccttagcg atgcaatcct cctatctgac      2100
atactgagag ttaatactga gattaccaag gcgccgttat ccgcttcaat gatcaaaagg      2160
tacgatgaac atcaccaaga cttgacactt ctcaaggccc tagtccgtca gcaactgcct      2220
gagaaatata aggaaatatt ctttgatcag tcgaaaaacg ggtacgcagg ttatattgac      2280
ggcggagcga gtcaagagga attctacaag tttatcaaac ccatattaga gaagatggat      2340
gggacggaag agttgcttgt aaaactcaat cgcgaagatc tactgcgaaa gcagcggact      2400
ttcgacaacg gtagcattcc acatcaaatc cacttaggcg aattgcatgc tatacttaga      2460
aggcaggagg atttttatcc gttcctcaaa gacaatcgtg aaaagattga gaaaatccta      2520
acctttcgca tacctactac tgtgggaccc ctggcccgag ggaactctcg gttcgcatgg      2580
atgacaagaa agtccgaaga aacgattact ccatggaatt ttgaggaagt tgtcgataaa      2640
ggtgcgtcag ctcaatcgtt catcgagagg atgaccaact ttgacaagaa tttaccgaac      2700
gaaaaagtat tgcctaagca cagtttactt tacgagtatt tcacagtgta caatgaactc      2760
acgaaagtta agtatgtcac tgagggcatg cgtaaacccg cctttctaag cggagaacag      2820
aagaaagcaa tagtagatct gttattcaag accaaccgca aagtgacagt taagcaattg      2880
aaagaggact actttaagaa aattgaatgc ttcgattctg tcgagatctc cggggtagaa      2940
gatcgattta atgcgtcact tggtacgtat catgacctcc taaagataat taaagataag      3000
gacttcctgg ataacgaaga gaatgaagat atcttagaag atatagtgtt gactcttacc      3060
ctctttgaag atcgggaaat gattgaggaa agactaaaaa catacgctca cctgttcgac      3120
gataaggtta tgaaacagtt aaagaggcgt cgctatacgg gctggggacg attgtcgcgg      3180
aaacttatca acgggataag agacaagcaa agtggtaaaa ctattctcga ttttctaaag      3240
agcgacggct tcgccaatag gaactttatg cagctgatcc atgatgactc tttaaccttc      3300
aaagaggata tacaaaaggc acaggtttcc ggacaagggg actcattgca cgaacatatt      3360
gcgaatcttg ctggttcgcc agccatcaaa aagggcatac tccagacagt caaagtagtg      3420
gatgagctag ttaaggtcat gggacgtcac aaaccggaaa acattgtaat cgagatggca      3480
cgcgaaaatc aaacgactca gaaggggcaa aaaaacagtc gagagcggat gaagagaata      3540
gaagagggta ttaaagaact gggcagccag atcttaaagg agcatcctgt ggaaaatacc      3600
```

-continued

```
caattgcaga acgagaaact ttacctctat tacctacaaa atggaaggga catgtatgtt    3660
gatcaggaac tggacataaa ccgtttatct gattacgacg tcgatcacat tgtaccccaa    3720
tcctttttga aggacgattc aatcgacaat aaagtgctta cacgctcgga taagaaccga    3780
gggaaaagtg acaatgttcc aagcgaggaa gtcgtaaaga aaatgaagaa ctattggcgg    3840
cagctcctaa atgcgaaact gataacgcaa agaaagttcg ataacttaac taaagctgag    3900
aggggtggct tgtctgaact tgacaaggcc ggatttatta aacgtcagct cgtggaaacc    3960
cgccaaatca caaagcatgt tgcacagata ctagattccc gaatgaatac gaaatacgac    4020
gagaacgata agctgattcg ggaagtcaaa gtaatcactt taaagtcaaa attggtgtcg    4080
gacttcagaa aggattttca attctataaa gttagggaga taaataacta ccaccatgcg    4140
cacgacgctt atcttaatgc cgtcgtaggg accgcactca ttaagaaata cccgaagcta    4200
gaaagtgagt ttgtgtatgg tgattacaaa gtttatgacg tccgtaagat gatcgcgaaa    4260
agcgaacagg agataggcaa ggctacagcc aaatacttct tttattctaa cattatgaat    4320
ttctttaaga cggaaatcac tctggcaaac ggagagatac gcaaacgacc tttaattgaa    4380
accaatgggg agacaggtga atcgtatgg gataagggcc gggacttcgc gacggtgaga    4440 aaagtttgt ccatgcccca agtcaacata gtaaagaaaa ctgaggtgca gaccggaggg    4500
ttttcaaagg aatcgattct tccaaaaagg aatagtgata agctcatcgc tcgtaaaaag    4560
gactgggacc cgaaaaagta cggtggcttc gatagcccta cagttgccta ttctgtccta    4620
gtagtggcaa aagttgagaa gggaaaatcc aagaaactga agtcagtcaa agaattattg    4680
gggataacga ttatggagcg ctcgtctttt gaaaagaacc ccatcgactt ccttgaggcg    4740
aaaggttaca aggaagtaaa aaaggatctc ataattaaac taccaaagta tagtctgttt    4800
gagttagaaa atggccgaaa acggatgttg gctagcgccg gagagcttca aaaggggaac    4860
gaactcgcac taccgtctaa atacgtgaat ttcctgtatt tagcgtccca ttacgagaag    4920
ttgaaaggtt cacctgaaga taacgaacag aagcaacttt tgttgagca gcacaaacat    4980 tatctcgacg aaatcataga gcaaatttcg gaattcagta agagagtcat cctagctgat    5040
gccaatctgg acaaagtatt aagcgcatac aacaagcaca gggataaacc catacgtgag    5100
caggcggaaa atattatcca tttgtttact cttaccaacc tcggcgctcc agccgcattc    5160
aagtattttg acacaacgat agatcgcaaa cgatacactt ctaccaagga ggtgctagac    5220
gcgacactga ttcaccaatc catcacggga ttatatgaaa ctcggataga tttgtcacag    5280 cttggggtg actctggtgg ttctcccaag aagaagagga aagtctaa                5328
```

<210> SEQ ID NO 2
<211> LENGTH: 22
<212> TYPE: DNA
<213> ORGANISM: Artificial Sequence
<220> FEATURE:
<223> OTHER INFORMATION: Ighg1

<400> SEQUENCE: 2
tcaacagcac tttccgttca gt                                              22

<210> SEQ ID NO 3
<211> LENGTH: 22
<212> TYPE: DNA
<213> ORGANISM: Artificial Sequence
<220> FEATURE:
<223> OTHER INFORMATION: Ighg2b

<400> SEQUENCE: 3

```
tacaacagta ctatccgggt gg                                              22

<210> SEQ ID NO 4
<211> LENGTH: 22
<212> TYPE: DNA
<213> ORGANISM: Artificial Sequence
<220> FEATURE:
<223> OTHER INFORMATION: Ighg2c

<400> SEQUENCE: 4
tacaacagta ctctccgggt gg                                              22

<210> SEQ ID NO 5
<211> LENGTH: 22
<212> TYPE: DNA
<213> ORGANISM: Artificial Sequence
<220> FEATURE:
<223> OTHER INFORMATION: Ighg3

<400> SEQUENCE: 5
tacaacagta ccttccgagt gg                                              22

<210> SEQ ID NO 6
<211> LENGTH: 20
<212> TYPE: DNA
<213> ORGANISM: Artificial Sequence
<220> FEATURE:
<223> OTHER INFORMATION: Ighg 1_ARMS_outer_F

<400> SEQUENCE: 6
tcccagaagt atcatctgtc                                                 20

<210> SEQ ID NO 7
<211> LENGTH: 15
<212> TYPE: DNA
<213> ORGANISM: Artificial Sequence
<220> FEATURE:
<223> OTHER INFORMATION: Ighg 1_ABEARMS F_14

<400> SEQUENCE: 7
ggaggagcag atcag                                                      15

<210> SEQ ID NO 8
<211> LENGTH: 15
<212> TYPE: DNA
<213> ORGANISM: Artificial Sequence
<220> FEATURE:
<223> OTHER INFORMATION: Ighg 1_ABE-A-ARMS R_15

<400> SEQUENCE: 8
aacggaaagt gctgt                                                      15

<210> SEQ ID NO 9
<211> LENGTH: 20
<212> TYPE: DNA
<213> ORGANISM: Artificial Sequence
<220> FEATURE:
<223> OTHER INFORMATION: Ighg 1_ARMS_outer_R

<400> SEQUENCE: 9
ctttggtttt ggagatggtt                                                 20

<210> SEQ ID NO 10
<211> LENGTH: 16
<212> TYPE: DNA
```

<213> ORGANISM: Artificial Sequence
<220> FEATURE:
<223> OTHER INFORMATION: Ighg 2b_ARMS_outer F

<400> SEQUENCE: 10
ctaacctcga gggtgg                                                       16

<210> SEQ ID NO 11
<211> LENGTH: 15
<212> TYPE: DNA
<213> ORGANISM: Artificial Sequence
<220> FEATURE:
<223> OTHER INFORMATION: Ighg 2b_ABEARMS R_14

<400> SEQUENCE: 11
atagagagga ttacg                                                        15

<210> SEQ ID NO 12
<211> LENGTH: 15
<212> TYPE: DNA
<213> ORGANISM: Artificial Sequence
<220> FEATURE:
<223> OTHER INFORMATION: Ighg 2b_ABE-A-ARMS R 15

<400> SEQUENCE: 12
ccggatagta ctgtt                                                        15

<210> SEQ ID NO 13
<211> LENGTH: 17
<212> TYPE: DNA
<213> ORGANISM: Artificial Sequence
<220> FEATURE:
<223> OTHER INFORMATION: Ighg 2b_ARMS_outer_R

<400> SEQUENCE: 13
ggcggcaaga tgtatac                                                      17

<210> SEQ ID NO 14
<211> LENGTH: 16
<212> TYPE: DNA
<213> ORGANISM: Artificial Sequence
<220> FEATURE:
<223> OTHER INFORMATION: Ighg 2c_ARMS_outer F

<400> SEQUENCE: 14
catgcgcagg taagtc                                                       16

<210> SEQ ID NO 15
<211> LENGTH: 15
<212> TYPE: DNA
<213> ORGANISM: Artificial Sequence
<220> FEATURE:
<223> OTHER INFORMATION: Ighg 2c_ABEARMS F_14

<400> SEQUENCE: 15
atagagagga ttacg                                                        15

<210> SEQ ID NO 16
<211> LENGTH: 15
<212> TYPE: DNA
<213> ORGANISM: Artificial Sequence
<220> FEATURE:
<223> OTHER INFORMATION: Ighg 2c_ABE-A-ARMS R_15

<400> SEQUENCE: 16
ccggagagta ctgtt                                                        15

<210> SEQ ID NO 17
<211> LENGTH: 20
<212> TYPE: DNA
<213> ORGANISM: Artificial Sequence
<220> FEATURE:
<223> OTHER INFORMATION: Ighg 2c_ARMS_outer_R

<400> SEQUENCE: 17
tgttgttgac cttgcatttg                                        20

<210> SEQ ID NO 18
<211> LENGTH: 20
<212> TYPE: DNA
<213> ORGANISM: Artificial Sequence
<220> FEATURE:
<223> OTHER INFORMATION: Ighg 3_ARMS_outer_F

<400> SEQUENCE: 18
ctggtaacat cttgggtgga                                        20

<210> SEQ ID NO 19
<211> LENGTH: 15
<212> TYPE: DNA
<213> ORGANISM: Artificial Sequence
<220> FEATURE:
<223> OTHER INFORMATION: Ighg 3_ABEARMS F_14

<400> SEQUENCE: 19
gtgaagctca gtacg                                             15

<210> SEQ ID NO 20
<211> LENGTH: 15
<212> TYPE: DNA
<213> ORGANISM: Artificial Sequence
<220> FEATURE:
<223> OTHER INFORMATION: Ighg 3_ABE-A-R_15

<400> SEQUENCE: 20
tcggaaggta ctgtt                                             15

<210> SEQ ID NO 21
<211> LENGTH: 19
<212> TYPE: DNA
<213> ORGANISM: Artificial Sequence
<220> FEATURE:
<223> OTHER INFORMATION: Ighg 3_ARMS_outer_R

<400> SEQUENCE: 21
ttcttcttgg acatttgtt                                         19

<210> SEQ ID NO 22
<211> LENGTH: 20
<212> TYPE: DNA
<213> ORGANISM: Artificial Sequence
<220> FEATURE:
<223> OTHER INFORMATION: IgG subclass_Ighg1_F

<400> SEQUENCE: 22
gcagcaccaa ggtggacaag                                        20

<210> SEQ ID NO 23
<211> LENGTH: 20
<212> TYPE: DNA
<213> ORGANISM: Artificial Sequence
<220> FEATURE:

<223> OTHER INFORMATION: IgG subclass_Ighg1_R

<400> SEQUENCE: 23
gtgctgggtg tggcagtgta                                                    20

<210> SEQ ID NO 24
<211> LENGTH: 20
<212> TYPE: DNA
<213> ORGANISM: Artificial Sequence
<220> FEATURE:
<223> OTHER INFORMATION: IgG subclass_Ighg2b_F

<400> SEQUENCE: 24
ctcctaactc cgagggtgga                                                    20

<210> SEQ ID NO 25
<211> LENGTH: 20
<212> TYPE: DNA
<213> ORGANISM: Artificial Sequence
<220> FEATURE:
<223> OTHER INFORMATION: IgG subclass_Ighg2b_R

<400> SEQUENCE: 25
gagatggttc ttccgatggg                                                    20

<210> SEQ ID NO 26
<211> LENGTH: 20
<212> TYPE: DNA
<213> ORGANISM: Artificial Sequence
<220> FEATURE:
<223> OTHER INFORMATION: IgG subclass_Ighg2c_F

<400> SEQUENCE: 26
accatccgtc ttcatcttcc                                                    20

<210> SEQ ID NO 27
<211> LENGTH: 20
<212> TYPE: DNA
<213> ORGANISM: Artificial Sequence
<220> FEATURE:
<223> OTHER INFORMATION: IgG subclass_Ighg2c_R

<400> SEQUENCE: 27
tgttgttgac cttgcatttg                                                    20

<210> SEQ ID NO 28
<211> LENGTH: 20
<212> TYPE: DNA
<213> ORGANISM: Artificial Sequence
<220> FEATURE:
<223> OTHER INFORMATION: IgG subclass_Ighg3_F

<400> SEQUENCE: 28
ctggtaacat cttgggtgga                                                    20

<210> SEQ ID NO 29
<211> LENGTH: 20
<212> TYPE: DNA
<213> ORGANISM: Artificial Sequence
<220> FEATURE:
<223> OTHER INFORMATION: IgG subclass_Ighg3_R

<400> SEQUENCE: 29
tgagatggtt ctctcgatgg                                                    20

<210> SEQ ID NO 30
<211> LENGTH: 20
<212> TYPE: DNA
<213> ORGANISM: Artificial Sequence
<220> FEATURE:
<223> OTHER INFORMATION: Fut8_Exon 9_F

<400> SEQUENCE: 30
accagtgtca atgcgagcat                                         20

<210> SEQ ID NO 31
<211> LENGTH: 20
<212> TYPE: DNA
<213> ORGANISM: Artificial Sequence
<220> FEATURE:
<223> OTHER INFORMATION: Fut8_Exon 9_R

<400> SEQUENCE: 31
tttcaagggc caggaagact                                         20

<210> SEQ ID NO 32
<211> LENGTH: 20
<212> TYPE: DNA
<213> ORGANISM: Artificial Sequence
<220> FEATURE:
<223> OTHER INFORMATION: Fut8_Exon 11_F

<400> SEQUENCE: 32
gtgaaaggtg ggaggagggt                                         20

<210> SEQ ID NO 33
<211> LENGTH: 23
<212> TYPE: DNA
<213> ORGANISM: Artificial Sequence
<220> FEATURE:
<223> OTHER INFORMATION: Fut8_Exon 11_R

<400> SEQUENCE: 33
tccagatgat tctcatgcat gct                                     23

<210> SEQ ID NO 34
<211> LENGTH: 20
<212> TYPE: DNA
<213> ORGANISM: Artificial Sequence
<220> FEATURE:
<223> OTHER INFORMATION: Fut8-e9-sgRNA#1

<400> SEQUENCE: 34
tactacctca gtcagacaga                                         20

<210> SEQ ID NO 35
<211> LENGTH: 20
<212> TYPE: DNA
<213> ORGANISM: Artificial Sequence
<220> FEATURE:
<223> OTHER INFORMATION: Fut8-e9-sgRNA#2

<400> SEQUENCE: 35
aaccagttct gtcagatctt                                         20

<210> SEQ ID NO 36
<211> LENGTH: 20
<212> TYPE: DNA
<213> ORGANISM: Artificial Sequence
<220> FEATURE:
<223> OTHER INFORMATION: Fut8-e11-sgRNA#1

```
<400> SEQUENCE: 36
cacccagcga acactcatct                                               20

<210> SEQ ID NO 37
<211> LENGTH: 22
<212> TYPE: DNA
<213> ORGANISM: Artificial Sequence
<220> FEATURE:
<223> OTHER INFORMATION: IgG2b

<400> SEQUENCE: 37
tacgacagta ctctccgggt gg                                            22

<210> SEQ ID NO 38
<211> LENGTH: 22
<212> TYPE: DNA
<213> ORGANISM: Artificial Sequence
<220> FEATURE:
<223> OTHER INFORMATION: IgG2c

<400> SEQUENCE: 38
tacgacagta ctctccgggt gg                                            22

<210> SEQ ID NO 39
<211> LENGTH: 22
<212> TYPE: DNA
<213> ORGANISM: Artificial Sequence
<220> FEATURE:
<223> OTHER INFORMATION: IgG3

<400> SEQUENCE: 39
tacgacagta ccttccgagt gg                                            22

<210> SEQ ID NO 40
<211> LENGTH: 22
<212> TYPE: DNA
<213> ORGANISM: Artificial Sequence
<220> FEATURE:
<223> OTHER INFORMATION: IgG1

<400> SEQUENCE: 40
tcagcagcac tttccgttca gt                                            22
```

TRANSGENIC MOUSE FOR AGLYCOSYLATED ANTIBODY PRODUCTION AND USE OF AGLYCOSYLATED ANTIBODY PRODUCED THEREFROM

TECHNICAL FIELD

The present disclosure relates to an aglycosylated antibody-producing transgenic mouse, a target antigen-specific aglycosylated antibody produced therefrom, and a method of diagnosing disease by analyzing a glycoprotein biomarker using the produced aglycosylated antibody.

The present disclosure was made with the support of the Korean government under grant number 1711064732 ("Development of Aglycosylated Antibody Production System through Gene Editing") awarded by the Ministry of Science and ICT.

Moreover, the present disclosure was made with the support of the Korean government under grant number NTM2371813 ("Development of Human Sugar Chain Mimicking Model Mice for Nonclinical Testing") awarded by the National Research Council of Science and Technology.

In addition, the present disclosure was made with the support of the Korean government under grant number KGM5181813 ("Main Project (2015-2018)") awarded by the Ministry of Science and ICT.

BACKGROUND ART

As markers for disease diagnosis, glycoproteins and disease-specific antigens have been used. For example, these markers include a prostate-specific antigen (PSA) of prostate cancer, a carcinoembryogenic antigen (CEA) of colorectal cancer, and alpha-fetoprotein (AFP) for diagnosis of testicular cancer and liver cancer, and the like. It is known that these markers increase quantitatively during disease progression, and sugar chains bound to proteins also change.

Immunoglobulin (Ig, antibody) is a reagent widely used in the field of disease diagnosis, and IgG-type antibodies occupy the largest share of the diagnostic market. IgG is composed of two heavy chains and two light chains linked by disulfide bonds. IgG is glycosylated at Asn297 in the CH2 constant domain of the heavy chain (N-glycosylation). N-glycosylation occurs in the consensus sequence Asn-X (except Pro)-Ser/Thr. In the field of disease diagnosis targeting glycoproteins, the sugar chain of IgG is an important factor that disturbs the diagnosis result. As an example, lectin is used to identify sugar chains such as glycoproteins, but may show cross-reaction with the sugar chains of IgG to confuse analysis results. In order to overcome this problem, efforts have been made to remove the sugar chain portion from the antibody, and a PNGase digestion method, a pepsin digestion method, a cross-linker method, and the like have been performed. However, these methods have limitations in that the efficiency of enzymatic and chemical reactions is not perfect, and it is difficult to retrieve IgG after treatment. Therefore, there is a need to fundamentally solve the sugar chain problem of the antibody.

The present inventors have modified the N-glycosylation sequence of the antibody into an aglycosylation sequence by editing the IgG gene in the genomic DNA of a mouse. In addition, the present inventors have produced an antibody from the mouse thus generated, have found that the produced antibody is an aglycosylated antibody, and have demonstrated that AFP-L3 can be quantitatively analyzed by ELISA and CLIA methods using the produced aglycoantibody, thereby completing the present disclosure.

DISCLOSURE

Technical Problem

An object of the present disclosure is to provide a recombinant expression vector comprising: a nucleotide sequence encoding at least one guide RNA (gRNA) that hybridizes to a DNA encoding an immunoglobulin G (IgG) protein; a nucleotide sequence encoding a Cas9 protein; a nucleotide sequence encoding an adenine base editor (ABE); and a promoter operably linked to the nucleotide sequences, or an RNA produced from the recombinant expression vector.

Another object of the present disclosure is to provide a transgenic cell line or embryo for generating an aglycosylated antibody-producing animal model, the transgenic cell line or embryo comprising the recombinant expression vector or the RNA.

Still another object of the present disclosure is to provide a method for generating an aglycosylated antibody-producing animal model, the method comprising a step of transferring the embryo into the oviduct of a non-human surrogate mother animal.

Yet another object of the present disclosure is to provide an aglycosylated antibody-producing animal model obtained by modification of immunoglobulin G (IgG) gene.

Still yet another object of the present disclosure is to provide a method for producing an aglycosylated antibody against an antigen, the method comprising a step of administering an antigen to be detected to the animal model.

A further object of the present disclosure is to provide an aglycosylated antibody produced by the method for producing an aglycosylated antibody.

Another further object of the present disclosure is to provide an immunoassay kit comprising: the aglycosylated antibody; and a glycoprotein biomarker.

Technical Solution

One aspect of the present disclosure provides a recombinant expression vector comprising: a nucleotide sequence encoding at least one guide RNA (gRNA) that hybridizes to a DNA encoding an immunoglobulin G (IgG) protein; a nucleotide sequence encoding a Cas9 protein; a nucleotide sequence encoding an adenine base editor (ABE); and a promoter operably linked to the nucleotide sequences, or an RNA produced from the recombinant expression vector.

According to one embodiment of the present disclosure, the IgG may be at least one subclass of IgG selected from the group consisting of IgG1, IgG2a, IgG2b, IgG2c and IgG3.

According to one embodiment of the present disclosure, the gRNA may comprise a nucleotide sequence complementary to any one sequence selected from the group consisting of SEQ ID NOs: 2 to 5.

Another aspect of the present disclosure provides a transgenic cell line or embryo for generating an aglycosylated antibody-producing animal model, the transgenic cell line or embryo comprising the recombinant expression vector or the RNA.

Still another aspect of the present disclosure provides a method for generating an aglycosylated antibody-producing animal model, the method comprising a step of transferring the embryo into the oviduct of a non-human surrogate mother animal.

According to one embodiment of the present disclosure, the animal may be a rabbit, a goat or a mouse.

According to one embodiment of the present disclosure, production of the aglycosylated antibody may comprise modification of at least one subclass of IgG selected from the group consisting of IgG1, IgG2a IgG2b, IgG2c and IgG3.

According to one embodiment of the present disclosure, the modification may comprise at least one substitution selected from the group consisting of: substitution of a sequence corresponding to SEQ ID NO: 2 with the sequence of SEQ ID NO: 40; substitution of a sequence corresponding to SEQ ID NO: 3 with the sequence of SEQ ID NO: 37; substitution of a sequence corresponding to SEQ ID NO: 4 with the sequence of SEQ ID NO: 38; and substitution of a sequence corresponding to SEQ ID NO: 5 with the sequence of SEQ ID NO: 39.

Yet another aspect of the present disclosure provides an aglycosylated antibody-producing animal model obtained by modification of immunoglobulin G (IgG) gene.

According to one embodiment of the present disclosure, the modification may comprise at least one substitution selected from the group consisting of: substitution of the amino acid N of an N-S-T sequence in the amino acid sequence of the IgG1 heavy chain with another amino acid; substitution of the amino acid N of an N-S-T sequence in the amino acid sequence of the IgG2a heavy chain with another amino acid; substitution of the amino acid N of an N-S-T sequence in the amino acid sequence of the IgG2b heavy chain with another amino acid; substitution of the amino acid N of an N-S-T sequence in the amino acid sequence of the IgG2c heavy chain with another amino acid; and substitution of the amino acid N of an N-S-T sequence in the amino acid sequence of the IgG3 heavy chain with another amino acid.

According to one embodiment of the present disclosure, the N-S-T sequence may be a sequence consisting of the $297^{th}$ to $299^{th}$ amino acids of the IgG heavy chain of any one selected from the group consisting of IgG1, IgG2a IgG2b, IgG2c and IgG3.

According to one embodiment of the present disclosure, the modification comprises at least one substitution selected from the group consisting of: substitution of a sequence corresponding to SEQ ID NO: 2 with the sequence of SEQ ID NO: 40; substitution of a sequence corresponding to SEQ ID NO: 3 with the sequence of SEQ ID NO: 37; substitution of a sequence corresponding to SEQ ID NO: 4 with the sequence of SEQ ID NO: 38; and substitution of a sequence corresponding to SEQ ID NO: 5 with the sequence of SEQ ID NO: 39.

According to one embodiment of the present disclosure, the animal may be not only a rabbit, a goat or a mouse, but also any animal capable of producing an antibody.

Still yet another aspect of the present disclosure provides a method for producing an aglycosylated antibody against an antigen, the method comprising a step of administering an antigen to be detected to the animal model.

A further aspect of the present disclosure provides an aglycosylated antibody produced by the method for producing an aglycosylated antibody.

Another further aspect of the present disclosure provides an immunoassay kit comprising: the aglycosylated antibody; and a glycoprotein biomarker.

According to one embodiment of the present disclosure, the glycoprotein biomarker may be detected by lectin.

According to one embodiment of the present disclosure, the lectin may be L4-PHA (phytohemagglutinin-L4), LCA (Lens culinaris agglutinin), DSA (Datura stramonium agglutinin), AAL (Aleuria aurantia agglutinin), selectin, Con A (concanavalin-A), WGA (wheat germ agglutinin), jacalin, SNA (Sambucus nigra agglutinin), or galectin.

According to one embodiment of the present disclosure, the glycoprotein may be AFP-L3.

Advantageous Effects

Using the transgenic mouse of the present disclosure, it is possible to easily produce aglycosylated antibodies against various target antigens, and to precisely diagnose disease by detecting a glycoprotein biomarker using the produced aglycosylated antibody.

BRIEF DESCRIPTION OF DRAWINGS

FIG. 1 is a schematic view showing that lectin may bind to a capture antibody even in the absence of an analyte.

FIG. 2 is a schematic view showing a method of analyzing a specific glycoform by ALIQUAT (Aglycosylated antibody-Lectin coupled Immunoassay for the QUAntification of Tumor marker), an immunoassay platform that uses an appropriate lectin and aglycosylated antibody.

FIG. 3 shows an N-S-T sequence commonly present in IgG2c, IgG2b, IgG1 and IgG3.

FIG. 4 is a schematic view showing a process of screening edited mutations using ARMS (amplification refractory mutation system) and PCR.

FIG. 5 shows the results of Sanger sequencing for IgG2c gene in nine pups born after the adenine base editing process.

FIG. 6 shows the results of Sanger sequencing for IgG2b gene in nine pups born after the adenine base editing process.

FIG. 7 shows the results of Sanger sequencing for IgG3 gene in nine pups born after the adenine base editing process.

FIG. 8 shows the nucleotide sequence of IgG2c edited according to adenine base editing.

FIG. 9 shows the nucleotide sequence of IgG2b edited according to adenine base editing.

FIG. 10 shows the nucleotide sequence of IgG3 edited according to adenine base editing.

FIG. 11 shows the results of Sanger sequencing for IgG2c and IgG3 in pup (#11).

FIG. 12 shows the results of analyzing the structure of IgG to select an intermediate founder. In FIG. 12(a), the wild-type IgG protein structure shows a conserved motif of N-S-T with the N-glycosylation to the Asn residue. FIG. 12(b) shows the hypothetical IgG2 structures of the mutant D-S-T and G-S-T antibody without N-glycosylation, wherein the G-S-T motif results in a structural alteration in the β-sandwich fold.

FIG. 13 shows the nucleotide sequence of IgG1 edited according to adenine base editing.

FIG. 14 shows that antibodies produced in a genome-edited mouse and a wild-type mouse, respectively, display an identical profile of IgG expression, whereas mice with knockout of IgG2b and IgG3 genes show defects in the production of the corresponding subclasses.

FIG. 15 shows a defect in the gene of the corresponding subclass in mice with knockout of IgG2b gene.

FIG. 16 shows a defect in the gene of the corresponding subclass in mice with knockout of IgG3 gene.

FIG. 17 is a graph showing an increased reactivity over time, as a result of performing direct ELISA assay against hAFP in serum collected in each immunization step after administering human AFP as a model antigen, which is a tumor marker for hepatocellular carcinoma, into the aglycosylated antibody-producing animal.

FIG. 18 shows hybridoma clones that produce an antibody that is highly specific to hAFP.

FIG. 19 shows that 1E5, 2A2 and 3A5 clones secrete a monoclonal antibody of the IgG1 subclass and kappa light chains.

FIG. 20 shows that the heavy chains of the 1E5 antibody have no N-glycans.

FIG. 21 shows aglycosylation of 1E5, 2A2 and 3A5 clones.

FIG. 22 shows the genotype of each FUT8$^{-/-}$ mutant cell line clone with a frame-shifted non-sense mutation.

FIG. 23 shows that FUT8$^{-/-}$ HEK293-T cells are resistant to PhoSL binding.

FIG. 24 shows the results of performing immunoblot analysis using an anti-hAFP antibody to visualize different glycoforms of AFP.

FIG. 25 shows mass analysis results indicating that AFP-L3 is absent in FUT8$^{-/-}$ cells and that the percent AFP-L3 produced in wild-type cells is 99.5%.

FIG. 26 shows standard curve analysis results for an aglycosylated antibody that shows good linearity compared to a validated commercial antibody in the range of 0 to 20 ng/ml AFP.

FIG. 27 is a graph showing that the lectin-ELISA assay using AAL and an aglycosylated antibody produced a standard curve with good sensitivity and linearity for L3-positive AFP samples.

FIG. 28 is a graph showing a standard curve having good linearity in the range of 0 to 100 ng/mL, obtained when an AFP-L3 standard molecule was spiked into a normal serum showing an AFP level of less than 1.0 ng/mL.

FIG. 29 is a graph showing %AFP-L3 values versus the AFP concentration, obtained through a lectin-ELISA hAFP test using an aglycosylated antibody and μ-TAS analysis.

FIG. 30 shows the stability of aglycosylated antibodies against thermal conditions.

FIG. 31 shows the stability of aglycosylated antibodies against pH conditions.

FIG. 32 shows the stability of aglycosylated antibodies against oxidative conditions.

BEST MODE

One aspect of the present disclosure provides a recombinant expression vector comprising: a nucleotide sequence encoding at least one guide RNA (gRNA) that hybridizes to a DNA encoding an immunoglobulin G (IgG) protein; a nucleotide sequence encoding a Cas9 protein; a nucleotide sequence encoding an adenine base editor (ABE); and a promoter operably linked to the nucleotide sequences, or an RNA produced from the recombinant expression vector.

The present specification provides: a method for generating an aglycosylated antibody-producing animal model, the method comprising a step of specifically modifying the IgG gene of a cell line or an embryo using an adenine base editing system, or transferring an embryo into the oviduct of a non-human surrogate mother animal, by application of a transgenic somatic cell cloning technique; a method for producing an aglycosylated antibody-producing transgenic animal; and the use of an aglycosylated antibody produced from the transgenic animal.

As used herein, the term "adenine base editing system" refers to a single-base editing induction system composed of a nickase Cas9-hypothetical deoxyadenosine deaminase fusion protein (adenine base editor; ABE) and a gRNA (guide RNA), which is a genome editing system designed to replace adenine of a desired gene nucleotide sequence with guanine without cleavage of DNA using a CRISPR (Clustered Regularly Interspaced Short Palindromic Repeats) and hypothetical deoxyadenosine deaminase system known as a microbial immune system.

As used herein, the term "adenine base editor (ABE)" is an essential protein element in the adenine base editing system, and is a nickase-Cas9 hypothetical deoxyadenosine deaminase fusion protein that may induce single base editing by forming a complex with gRNA. The ABE protein may be one developed by David R. Liu in 2017.

As used herein, the term "base editor" refers to a protein that more efficiently mediates modification in genomic DNA than the existing CRISPR/Cas9 system, and is specifically used in a base editing system capable of 'G-C' to A-T' or 'A-T to G-C' conversion. In the present disclosure, among others, modification of the IgG gene was induced using an adenine base editor that induces particularly 'A-T to G-C' conversion.

As used herein, the term "gRNA" refers to an RNA comprising a nucleotide sequence capable of binding complementarily to a target DNA. Specifically, gRNA refers to a single-stranded RNA that may form a complex with a Cas9 protein or the nickase-Cas9 protein and may direct the Cas9 protein or the adenine base editor protein to a target DNA.

When an embryo or a cell is transformed with the recombinant expression vector or RNA of the present disclosure, a gRNA fragment may be delivered into the cell, and the delivered gRNA fragment may recognize an IgG gene. Therefore, when an embryo or a cell is transformed with the recombinant expression vector or the RNA, gRNA may be delivered into the cell, and the delivered gRNA may serve to form a structure that may be recognized by the adenine base editor or the Cas9 protein complex.

As used herein, the term "modification" refers to converting a portion of a nucleotide sequence, which encodes a specific amino acid, into a sequence encoding another amino acid.

As used herein, the term "recombinant expression vector" refers to a recombinant DNA molecule containing a desired coding sequence and appropriate nucleic acid sequences necessary for the expression of the operably linked coding sequence in a particular host organism. Promoters, enhancers, and termination and polyadenylation signals, which may be used in eukaryotic cells, are known.

As used herein, the term "operably linked" refers to a functional linkage between a gene expression control sequence and another nucleotide sequence. The gene expression control sequence may be at least one selected from the group consisting of a replication origin, a promoter, and a transcription termination sequence (terminator). The transcription termination sequence may be a polyadenylation sequence (pA), and the replication origin may be an f1 replication origin, an SV40 replication origin, a pMB1 replication origin, an adeno replication origin, an AAV replication origin or a BBV replication origin, but is not limited thereto.

As used herein, the term "promoter" means a region of DNA upstream from the structural gene, and refers to a DNA molecule to which RNA polymerase binds to initiate transcription.

The promoter according to one embodiment of the present disclosure is one of the transcription control sequences which regulate the transcription initiation of a specific gene, and may be a polynucleotide fragment of about 100 to about 2,500 bp in length. The promoter can be used without limitation as long as it can regulate transcription initiation in cells, for example, eukaryotic cells (e.g., plant cells or animal cells (e.g., mammalian cells such as human or mouse cells)). For example, the promoter may be selected from the group consisting of cytomegalovirus (CMV) promoter (e.g., human or mouse CMV immediate-early promoter), U6 promoter, EF1-alpha (elongation factor 1-a) promoter, EF1-alpha short (EFS) promoter, SV40 promoter, adenovirus promoter (major late promoter), pLλ promoter, trp promoter, lac promoter, tac promoter, T7 promoter, vaccinia virus 7.5K promoter, HSV tk promoter, SV40E1 promoter, respiratory syncytial virus (RSV) promoter, metallothionin promoter, β-actin promoter, ubiquitin C promoter, human interleukin-2 (IL-2) gene promoter, human lymphotoxin gene promoter, and human granulocyte-macrophage colony stimulating factor (GM-CSF) gene promoter, but is not limited thereto.

The recombinant expression vector according to one embodiment of the present disclosure may be selected from the group consisting of plasmid vectors, cosmid vectors, and viral vectors such as bacteriophage vectors, adenovirus vectors, retroviral vectors, and adeno-associated viral vectors. A vector that may be used as the recombinant expression vector may be constructed based on, but not limited to, a plasmid (e.g., pcDNA series, pSC101, pGV1106, pACYC177, ColE1, pKT230, μME290, pBR322, pUC8/9, pUC6, pBD9, pHC79, pIJ61, pLAFR1, pHV14, pGEX series, pET series, pUC19, etc.), a phage (e.g., λgt4λB, λ-Charon, λΔz1, M13, etc.), a viral vector (e.g., an adeno-associated viral (AAV) vector, etc.), or the like, which is used in the art.

The recombinant expression vector of the present disclosure may further comprise at least one selectable marker. The marker is generally a nucleic acid sequence having the property of being selected by a common chemical method, and includes any gene capable of distinguishing a transfected cell from a non-transfected cell. Examples of the marker include, but are not limited to, genes resistant to herbicides such as glyphosate, glufosinate ammonium or phosphinothricin, and genes resistant to antibiotics such as ampicillin, kanamycin, G418, bleomycin, hygromycin or chloramphenicol.

The recombinant expression vector of the present disclosure may be constructed using a gene recombination technique well known in the art, and site-specific DNA cleavage and ligation may be performed using enzymes generally known in the art.

"RNA" produced from the recombinant expression vector of the present disclosure refers to an mRNA synthesized in vitro using the recombinant expression vector as a template.

According to one embodiment of the present disclosure, the IgG may be at least one subclass of IgG selected from the group consisting of IgG1, IgG2a, IgG2b, IgG2c and IgG3.

An aglycosylated antibody may be produced from the mouse by modification of the mouse IgG gene, specifically IgG1, IgG2a, IgG2b, IgG2c and/or IgG3, preferably modification of all IgG1, IgG2b, IgG2c and IgG3. In addition, it is possible to establish an aglycosylated antibody-producing mouse system by fixing the modified IgG gene by repeated backcrossing of mice.

According to one embodiment of the present disclosure, the gRNA may comprise a nucleotide sequence complementary to any one sequence selected from the group consisting of SEQ ID NOs: 2 to 5.

Another aspect of the present disclosure provides a transgenic cell line or embryo for generating an aglycosylated antibody-producing animal model, the transgenic cell line or embryo comprising the recombinant expression vector or the RNA.

In order to produce a transgenic embryo comprising the recombinant expression vector or RNA according to one embodiment of the present disclosure, the embryo was obtained by crossing wild-type C57BL/6 mice, but is not limited thereto. A method known in the art for introducing a nucleic acid molecule into a fertilized egg or an embryo may be used, and as known in the art, a suitable standard technique may be selected and performed. Examples of this method include, but are not limited to, electroporation, microinjection, and the like.

In order to produce a transgenic cell line comprising the recombinant expression vector or RNA according to one embodiment of the present disclosure, a method known in the art for introducing a nucleic acid molecule into an organism, a cell, a tissue or ab organ may be used, and as known in the art, a suitable standard technique may be selected according to the host cell and used. Examples of this method include, but are not limited to, electroporation, calcium phosphate ($CaPO_4$) precipitation, calcium chloride ($CaCl_2$) precipitation, microinjection, polyethylene glycol (PEG) method, DEAE-dextran method, cationic liposome method, and lithium acetate-DMSO method.

The type of cell to be used as the transgenic cell line may be animal cells or cells derived from animal cells, preferably mammals, preferably animals used for antibody production, such as mice, rabbits and goats, or somatic cells or fertilized eggs and embryos derived from these animals, most preferably mice or somatic cells or fertilized eggs or embryos derived from mice. When mouse-derived somatic cells are used as the transgenic cell line, it is possible to overcome the problem of mice dying immediately after birth.

Still another aspect of the present disclosure provides a method for generating an aglycosylated antibody-producing animal model, the method comprising a step of transferring the embryo into the oviduct of a non-human surrogate mother animal.

The method for generating an aglycosylated antibody-producing animal model may be performed by somatic cell nuclear transfer (SCNT). "Somatic cell nuclear transfer" is a gene manipulation technique capable of producing offspring without passing through meiotic and haploid germ cells, which generally occur in the reproductive process, and is a method comprising transferring a polyploid somatic cell of an adult into an enucleated oocyte to produce an embryo, and transferring the embryo into a living body to generate a new individual.

As used herein, the term "nuclear transfer embryo" refers to an oocyte produced by insertion or fusion of a nuclear donor cell, and "fusion" refers to a combination of a nuclear donor cell and a lipid membrane portion of an oocyte. For example, the lipid membrane may be the plasma membrane or nuclear membrane of a cell. Fusion may occur upon application of an electrical stimulus between a nuclear donor cell and a recipient oocyte when they are placed adjacent to each other or when a nuclear donor cell is placed in a perivitelline space of a recipient oocyte. The term "transgenic cell line" refers to a nuclear donor cell, which transfers to the nuclear recipient oocyte, or a nucleus of the cell. The term "oocyte" preferably refers to a mature oocyte which has reached metaphase II of meiosis, preferably a mouse oocyte.

According to one embodiment of the present disclosure, the animal may be a rabbit, a goat or a mouse, but is not limited thereto.

Mice have already been used in research on pathological mechanisms and treatment of various diseases, and particularly, have been recognized as an economic animal for a long time, and thus the use thereof can avoid ethical problems, unlike when other medium/large animals are used as disease models. In addition, since a stable breeding system for mice is already established, mice are advantageously easy to maintain and control during development of an experimental animal model. In addition, rabbits and goats have already been used in various manners for antibody production, and thus may be easily used for the production of the aglycosylated antibody of the present disclosure. Other animals such as chickens, horses, etc. that can produce antibodies may also be used.

According to one embodiment of the present disclosure, production of the aglycosylated antibody may comprise modification of at least one subclass of IgG selected from the group consisting of IgG1, IgG2a IgG2b, IgG2c and IgG3.

The aglycosylated antibody-producing animal model may be generated through modification of IgG by substitution of a portion of nucleotides constituting the IgG gene.

According to one embodiment of the present disclosure, the modification may comprise at least one substitution selected from the group consisting of: substitution of a sequence corresponding to SEQ ID NO: 2 with the sequence of SEQ ID NO: 40; substitution of a sequence corresponding to SEQ ID NO: 3 with the sequence of SEQ ID NO: 37; substitution of a sequence corresponding to SEQ ID NO: 4 with the sequence of SEQ ID NO: 38; and substitution of a sequence corresponding to SEQ ID NO: 5 with the sequence of SEQ ID NO: 39.

Yet another aspect of the present disclosure provides an aglycosylated antibody-producing animal model obtained by modification of immunoglobulin G (IgG) gene.

In the aglycosylated antibody-producing animal model of the present disclosure, contents overlapping with the above description may be used in the same sense as described above.

According to one embodiment of the present disclosure, the modification may comprise at least one substitution selected from the group consisting of: substitution of at least one amino acid of an N-S-T sequence in the amino acid sequence of the IgG1 heavy chain with another amino acid; substitution of at least one amino acid of an N-S-T sequence in the amino acid sequence of the IgG2b heavy chain with another amino acid; substitution of at least one amino acid of an N-S-T sequence in the amino acid sequence of the IgG2c heavy chain with another amino acid; and substitution of at least one amino acid of an N-S-T sequence in the amino acid sequence of the IgG3 heavy chain with another amino acid.

More preferably, the modification may comprise at least one substitution selected from the group consisting of: substitution of the amino acid N of an N-S-T sequence in the amino acid sequence of the IgG1 heavy chain with an amino acid other than N, or substitution of S with P, or substitution of T with an amino acid other than S; substitution of the amino acid N of an N-S-T sequence in the amino acid sequence of the IgG2b heavy chain with an amino acid other than N, or substitution of S with P, or substitution of T with an amino acid other than S; substitution of the amino acid N of an N-S-T sequence in the amino acid sequence of the IgG2c heavy chain with an amino acid other than N, or substitution of S with P, or substitution of T with an amino acid other than S; and substitution of the amino acid N of an N-S-T sequence in the amino acid sequence of the IgG3 heavy chain with an amino acid other than N, or substitution of S with P, or substitution of T with an amino acid other than S.

The mutation of N-S-T into D-S-T is more preferable than the mutation into D-G-T or G-S-T. This is because the N-glycosylation asparagine residue is located at the exposed loop between two strands of the immunoglobulin β-sandwich fold, and thus aspartic acid that exhibits an identical geometry to that of asparagine can avoid potential geometrical instability, unlike glycine (GST), even though it has a charged side chain.

According to one embodiment of the present disclosure, the N-S-T sequence may be a sequence consisting of the $297^{th}$ to $299^{th}$ amino acids of the IgG heavy chain of any one selected from the group consisting of IgG1, IgG2a IgG2b, IgG2c and IgG3.

According to one embodiment of the present disclosure, the modification may comprise at least one substitution selected from the group consisting of: substitution of a sequence corresponding to SEQ ID NO: 2 with the sequence of SEQ ID NO: 40; substitution of a sequence corresponding to SEQ ID NO: 3 with the sequence of SEQ ID NO: 37; substitution of a sequence corresponding to SEQ ID NO: 4 with the sequence of SEQ ID NO: 38; and substitution of a sequence corresponding to SEQ ID NO: 5 with the sequence of SEQ ID NO: 39.

According to one embodiment of the present disclosure, the animal may be a rabbit, a goat or a mouse, but is not limited thereto.

Still yet another aspect of the present disclosure provides a method for producing an aglycosylated antibody against an antigen, the method comprising a step of administering an antigen to be detected to the animal model.

According to one embodiment of the present disclosure, the method for producing an aglycosylated antibody may comprise a process of separating and purifying the aglycosylated antibody from the transgenic mouse after administering the antigen. Separation and purification of the antibody may be performed using a method known in the art, such as separation using a column, or separation using protein G agarose beads, but is not limited thereto.

A further aspect of the present disclosure provides an aglycosylated antibody produced by the method for producing an aglycosylated antibody.

The aglycosylated antibody produced by the method of the present disclosure is an antibody in which a sugar chain is not added to the heavy chain of the antibody, that is, an antibody that does not undergo a glycosylation reaction. Accordingly, cross-linking of the antibody with a sugar chain portion may be excluded, and thus the antibody may be effectively used in various molecular biological assays for sugar chain studies and kits for diagnosis of diseases.

Another further aspect of the present disclosure provides an immunoassay kit comprising: the aglycosylated antibody; and a glycoprotein biomarker.

The immunoassay kit of the present disclosure may comprise, for example, an immunodiagnostic strip. The strip may comprise, but is not limited to: a sample pad configured to absorb a biological sample; a conjugation pad comprising an aglycosylated antibody that binds specifically to a disease antigen to be detected which is present in the biological sample; a test membrane comprising a test line on which the aglycosylated antibody that binds specifically to the disease antigen to be detected is immobilized and a control line on which a control antibody is immobilized; and an absorption pad configured to absorb the sample remaining after the reaction between the biological sample and each of the antibodies. In addition, the strip may further comprise reagents that are commonly used in immunodiagnosis in the art.

The term "glycoprotein" refers to a complex protein in which 2 to 6 types of monosaccharides and proteins are covalently linked. Glycoproteins are present in almost all cells in vivo. It is known that glycoproteins detect and recognize extracellular signals, function to carry chemicals, and are involved in various inflammations and diseases. Thus, it is possible to diagnose various diseases by analyzing glycoproteins.

As used herein, the term "immunoassay" refers to a method of detecting disease infection, disease onset, disease progression, etc., based on a specific antigen-antibody reaction. Examples of the immunoassay include, but are not limited to, enzyme immunoassay, fluorescence immunoassay, and the like.

According to one embodiment of the present disclosure, the glycoprotein biomarker may be detected by a lectin.

The term "lectin" as used herein refers to a protein that specifically binds to a specific sugar molecule. The lectin may be one used to identify proteins modified with sugar chains in the field of molecular diagnostics.

According to one embodiment of the present disclosure, the lectin may be L4-PHA (phytohemagglutinin-L4), LCA (Lens culinaris agglutinin), DSA (Datura stramonium agglutinin), AAL (Aleuria aurantia agglutinin), selectin, Con A (concanavalin-A), WGA (wheat germ agglutinin), jacalin, SNA (Sambucus nigra agglutinin), or galectin, but is not limited thereto.

According to one embodiment of the present disclosure, the glycoprotein may be AFP-L3, but may also include a biomarker that is specifically effective for diagnosis of a specific disease.

It is known that the level of AFP-L3 increases in liver cancer patients, and the level of CA-125 (mucin 16, MUC16) increases in liver cirrhosis patients and ovarian cancer patients. Since the lectin cannot bind to the aglycosylated antibody, the presence and amount of a glycoprotein contained in a biological sample may be accurately measured using the kit of the present disclosure. Specifically, in the present disclosure, it was specifically confirmed that reliable diagnosis of liver cancer is possible by measuring the amount of AFP-L3 using AAL as an aglycosylated antibody produced from the aglycosylated antibody-producing animal model of the present disclosure.

According to an embodiment of the present disclosure, the method of analyzing a glycoprotein using the immunoassay kit of the present disclosure may be performed an additional protein analysis method known in the art, and examples of this additional method include, but are not limited to, Western blot assay, ELISA (enzyme-linked immunosorbent assay), radioimmunoassay (otA), radial immunodiffusion, electrophoresis, immunoprecipitation assay, FACS, and protein chip assay.

Mode for Invention

Hereafter, the present disclosure will be described in more detail with reference to one or more examples. However, these examples serve to explain the present disclosure by way of example, and the scope of the present disclosure is not limited to these examples.

EXAMPLE 1

Methods for Generation and Evaluation of Aglycosylated Antibody-Producing Mice 1-1. Animal Preparation Procedures for the use and care of animals were reviewed and approved by the Institutional Animal Care and Use Committee (IACUC), KRIBB. Zygotes were obtained from C57BL/6J mice and ICR female mice were used as recipients. Gene-edited C57BL/6J mice were back-crossed with Balb/c mice. All animals were bred in a pathogen-free facility with a constant temperature of 24° C., humidity of 40%, and 12-hr light/12-hr dark cycles.

1-2. Preparation of ABE (Adenine Base Editor) mRNA

The pCMV-ABE7.10 (Addgene, #102919) and xCas9 (3.7)-ABE(7.10) (Addgene, #108382) plasmid vectors were purchased from Addgene. The plasmids were digested with AgeI (NEB) for 2 hours at 37° C. and the linearized vectors were purified using a PCR purification kit (Qiagen). 1 µg of the purified vector was used as a template for mRNA synthesis using an mMESSAGE mMACHINE T7 Ultra kit (Thermo Fisher Scientific). mRNA was isolated using the MEGAclear kit (Thermo Fisher Scientific) and aliquoted in cryotube vials, and then stored in liquid nitrogen. The nucleotide sequence of ABE used is shown in Table 1 below.

TABLE 1

ABE; SEQ ID NO: 1 ggaaaatattatccatttgtttactcttaccaacctcggcgctccagccg
cattcaagtattttgacacaacgatagatcgcaaacgatacacttctacc
aaggaggtgctagacgcgacactgattcaccaatccatcacgggattata
tgaaactcggatagatttgtcacagcttgggggtgactctggtggttctc
ccaagaagaagaggaaagtctaa 1-3. Genome Editing and Zygote Transplantation by Microinjection and Electroporation hCG hormone (5IU) was injected into the peritoneal cavity of C57BL/6J female mice (5 weeks old) at 48-hour intervals after injection of PMSG hormone (5IU, Merck). Female mice were mated with 9-week-old C57BL/6J male mice and one-cell zygotes were collected from the ampulla of the oviduct of female mice. Cumulus cells were removed by incubation in M2 media containing 3 mg/ml hyaluronidase (Merck). A mixture comprising 3 µg/µl ABE mRNA having the nucleotide sequence shown in Table 1 of Example 1-2 and 3 µg/µl sgRNA (Toolgen, Korea) for binding to target DNA was micro-injected into the cytoplasm of zygotes using a Femtojet microinjector (Eppendorf, Germany) with an LEICA DMIRB manipulator (Leica Microsystems).

TABLE 2

| Name | CRISPR-targeting nucleotide sequence (5'→3') | SEQ ID NO |
|---|---|---|
| Ighg1 | TCAACAGCACTTTCCGTTC AGT | SEQ ID NO: 2 |
| Ighg2b | TACAACAGTACTATCCGGG TGG | SEQ ID NO: 3 |
| Ighg2c | TACAACAGTACTCTCCGGG TGG | SEQ ID NO: 4 |
| Ighg3 | TACAACAGTACCTTCCGAG TGG | SEQ ID NO: 5 |

Meanwhile, for genome editing, an electroporation mixture was prepared by dissolving 500 ng/µl sgRNA and 400 ng/µl ABE mRNA (prepared in Example 1-2) in opti-MEM (Gibco). Zygotes were suspended in the electroporation mixture and subjected to electroporation using a NEPA 21 electroporator (NEPA GENE) according to the manufacturer's protocol.

After microinjection or electroporation, zygotes were incubated in KSOM+AA medium (Millipore) at 37° C. in an incubator supplemented with 5% $CO_2$ and cultured until the two-cell stage. Then, the viable cells were transplanted into the oviducts of pseudo-pregnant recipient mice.

1-4. Genotyping

The toes were dissected from 1-week-old pups to isolate genomic DNA.

1-5. Preparation of Hybridoma Cells

An antigenic solution was prepared by dissolving 50 μg of human AFP (Mybiosource) in 100 μl of TiterMax Gold adjuvant (Merck), and was injected into the footpad of genome-edited mice (6 weeks old) four times at 1 week-intervals. After the final injection, the popliteal lymph nodes were dissected, and B cells were collected and then fused with myeloma FO cells according to a conventional method. A single fused cell was placed in a culture dish and cultured in a medium supplemented with 20% FBS, 1× HAT (100 μM hypoxanthine, 0.4 μM aminopterin, and 16 μM thymidine) (Merck), and 1× antibiotic-antimycotic solution (100 units/

TABLE 3

| Primer | Primer nucleotide sequence (5'→3') | PCR product size (bp) Control | A | G | SEQ ID NO |
|---|---|---|---|---|---|
| Ighg 1_ARMS_outer_F | TCCCAGAAGTATCATCTGTC | 321 | 203 | 147 | SEQ ID NO: 6 |
| Ighg 1_ABE+G-ARMS F_14+G | GGAGGAGCAGATCAG | | | | SEQ ID NO: 7 |
| Ighg 1_ABE-A-ARMS R_15 | AACGGAAAGTGCTGT | | | | SEQ ID NO: 8 |
| Ighg 1_ARMS_outer_R | CTTTGGTTTTGGAGATGGTT | | | | SEQ ID NO: 9 |
| Ighg 2b_ARMS_outer F | CTAACCTCGAGGGTGG | 476 | 209 | 296 | SEQ ID NO: 10 |
| Ighg 2b_ABE+G-ARMS R_14+G | ATAGAGAGGATTACG | | | | SEQ ID NO: 11 |
| Ighg 2b_ABE-A-ARMS R 15 | CCGGATAGTACTGTT | | | | SEQ ID NO: 12 |
| Ighg 2b_ARMS_outer_R | GGCGGCAAGATGTATAC | | | | SEQ ID NO: 13 |
| Ighg 2c_ARMS_outer F | CATGCGCAGGTAAGTC | 403 | 330 | 102 | SEQ ID NO: 14 |
| Ighg 2c_ABE+G-ARMS F_14+G | ATAGAGAGGATTACG | | | | SEQ ID NO: 15 |
| Ighg 2c_ABE-A-ARMS R_15 | CCGGAGAGTACTGTT | | | | SEQ ID NO: 16 |
| Ighg 2c_ARMS_outer_R | TGTTGTTGACCTTGCATTTG | | | | SEQ ID NO: 17 |
| Ighg 3_ARMS_outer_F | CTGGTAACATCTTGGGTGGA | 506 | 212 | 323 | SEQ ID NO: 18 |
| Ighg 3_ABE+G-ARMS F_14+G | GTGAAGCTCAGTACG | | | | SEQ ID NO: 19 |
| Ighg 3_ABE-A-R_15 | TCGGAAGGTACTGTT | | | | SEQ ID NO: 20 |
| Ighg 3_ARMS_outer_R | TTCTTCTTGGACATTTGTT | | | | SEQ ID NO: 21 |

For single base editing, pre-screening of genotypes was performed using the primers shown in Table 3 above by ARMS (amplification refractory mutation system) using H-Taq (Biofact), and the samples with only a guanine band at the target site were subjected to Sanger sequencing analysis. The target loci were PCR-amplified using Pfu and specific primers (Table 4), and the final mutation was confirmed by Sanger sequencing of PCR products.

ml penicillin, 100 μg/ml streptomycin sulfate, and 0.25 μg/ml amphotericin B) (Welgene, Korea) for 2 weeks. Positive clones that produced antibodies against hAFP were screened using indirect ELISA tests. Human AFP solutions were prepared by dissolving hAFP in PBS at a concentration of 1 μg/ml. Antigen solutions (100 μl) were used to coat the surface of 96-well plate (Thermo Fisher Scientific). After blocking, the culture-conditioned media were diluted 100-

TABLE 4

| Primer | | Primer nucleotide sequence (5'→3') | SEQ ID NO |
|---|---|---|---|
| IgG subclass_Ighg1 | Forward | GCAGCACCAAGGTGGACAAG | SEQ ID NO: 22 |
| | Reverse | GTGCTGGGTGTGGCAGTGTA | SEQ ID NO: 23 |
| IgG subclass_Ighg2b | Forward | CTCCTAACTCCGAGGGTGGA | SEQ ID NO: 24 |
| | Reverse | GAGATGGTTCTTCCGATGGG | SEQ ID NO: 25 |
| IgG subclass_Ighg2c | Forward | ACCATCCGTCTTCATCTTCC | SEQ ID NO: 26 |
| | Reverse | TGTTGTTGACCTTGCATTTG | SEQ ID NO: 27 |
| IgG subclass_Ighg3 | Forward | CTGGTAACATCTTGGGTGGA | SEQ ID NO: 28 |
| | Reverse | TGAGATGGTTCTCTCGATGG | SEQ ID NO: 29 |
| Fut8_Exon 9 | Forward | ACCAGTGTCAATGCGAGCAT | SEQ ID NO: 30 |
| | Reverse | TTTCAAGGGCCAGGAAGACT | SEQ ID NO: 31 |
| Fut8_Exon 11 | Forward | GTGAAAGGTGGGAGGAGGGT | SEQ ID NO: 32 |
| | Reverse | TCCAGATGATTCTCATGCATGCT | SEQ ID NO: 33 | fold, added to wells of the coated well plates and then incubated therein. After washing three times with TBS-Tween-20 (0.02%), treatment with anti-mouse secondary antibody conjugated with horseradish peroxidase (HRP) (Cell Signaling Technology, diluted at 1:2000) was performed, followed by treatment with TMB-ultra solution (Thermo Fisher Scientific). The chemical reaction was halted by adding 100 μl of 0.2N $H_2SO_4$, and then the absorbance at 450 nm was measured using a VERSA max microplate reader (Molecular Devices). The positive clones were cultured in serum-free media (Gibco) to produce aglycosylated monoclonal antibodies.

1-6. Production of Monoclonal Antibodies

The hybridoma cells prepared in Example 1-5 were cultured in serum-free media (Gibco) with agitation at 100 RPM in a chamber supplemented with 5% $CO_2$ for 72 hours. The conditioned media were collected, and cell debris was removed by centrifugation at 13,000 g for 30 minutes. The remaining debris was removed by filtration through a 0.22-μm syringe filter (Millipore). The filtrates were purified with a HiTrap™ Protein G HP column (GE Healthcare Life Sciences) using an FPLC system (AKTA purifier, GE Healthcare Life Sciences). The column was equilibrated with PBS (phosphate-buffered saline), and the filtrates were passed through the column at a flow rate of 1 min/ml, and bound proteins were eluted with 50 mM glycine-HCl (pH 2.5) at a flow rate of 3 ml/min. The eluted fractions were neutralized with 1M Tris-HCl (pH 8.0) and then mixed with a protein-stabilizing cocktail solution (Thermo Fisher Scientific), followed by storage at −20° C.

1-7. Preparation of FUT8 Knockout Cells

FUT8-targeting guide RNA constructs (Table 5) were generated by cloning hybridized oligonucleotide pairs into the pSpCas9(BB)-2A-Puro (PX459) vector (Addgene plasmid #48139).

of a sample was 2000 ng/ml or higher, the sample was manually diluted based on the previous results according to the manufacturer's instructions. All testing was conducted at the Pusan National University Yangsan Hospital, and no information on the subjects was provided before testing.

1-9. Immunofluorescence Assay

Edited HEK293-T cells ($2 \times 10^4$) were allowed to grow for 1 day on 18 mm×18 mm cover glass in DMEM media. Cells were fixed with BD cytofix/cytoperm solution (BD Biosci-ence) for 12 hours. Cells were then incubated in the presence of 9 ng/μl PhoSL-Alexa 488 for 2 hours at room temperature. After washing three times with PBS, cover glass was sealed in Vectashield mounting medium (Vector Laboratories) containing 1.5 μg/ml DAPI. Fluorescence was monitored on a Zeiss LSM510 Meta microscope (Carl Zeiss MicroImaging).

1-10. Sandwich Lectin-ELISA

ELISA well plates were coated with 0.5 μg of either anti-hAFP mouse monoclonal antibody (#ab54745, Abcam) or anti-hAFP aglycosylated antibodies dissolved in 0.1M sodium bicarbonate buffer (pH 7.4) at 4° C. overnight. The plates were washed twice with TBS-0.1% Tween-20 and blocked with protein-free blocking buffer (Thermo Fisher Scientific) and 0.5% polyvinyl alcohol plus 0.1% Tween-20 for 1 hour at room temperature. Clinical samples or culture media (100 μl) were dispensed into each well. Each well was washed with RIPA buffer (25 mM Tris-HCl 7.6, 150 mM NaCl, 1% NP40, 1% sodium deoxycholate, 0.1% SDS) at least five times and again with TBS-T. Then, each well was treated with either an anti-hAFP rabbit polyclonal antibody (#ab8201, Abcam) diluted at 1:2000 or biotin-labeled AAL (*Aleuria aurantia* lectin) (#B-1395, VECTOR Laboratories) diluted at 1:1000, for 1 hour at room temperature. After sufficient washing, each well was treated with a 1:2000 dilution of an anti-rabbit secondary antibody (Cell Signal-

TABLE 5

| Name | CRISPR-targeting nucleotide sequence (5'→3') | SEQ ID NO |
|---|---|---|
| Fut8-e9-sgRNA#1 | TACTACCTCAGTCAGACAGA | SEQ ID NO: 34 |
| Fut8-e9-sgRNA#2 | AACCAGTTCTGTCAGATCTT | SEQ ID NO: 35 |
| Fut8-e11-sgRNA#1 | CACCCAGCGAACACTCATCT | SEQ ID NO: 36 |

Specifically, 10 μg of the vector was digested with 50 units of BbsI for 1 hour, and digested vectors were gel-extracted using a gel-extraction kit (Solgent) and then the paired gRNA (10 pmol) was cloned into the linearized vector. The target sequence was confirmed by Sanger sequencing. The vector construct (10 μg) was used to transfect HEK293-T cells ($8 \times 10^5$ cells) using an electroporator (Neon, Invitrogen) with the following parameters: voltage 1300V, pulse width 10 ms, and pulse number 3. A single cell was placed in each well to form a clone, and genotyping of each clone was performed by Sanger sequencing to screen the FUT8$^{-/-}$ clones.

1-8. μ-Tas Analysis

The alpha-fetoprotein AFP-L3 was measured in the remnant serum samples using microchip capillary electrophoresis and liquid-phase binding assay on an automatic analyzer (mTAS Wako i30, Wako Pure Chemical Industries, Osaka, Japan). The measurement range was 0.3 to 2000 ng/ml for AFP, and the AFP-L3 levels were calculated in sera whose AFP levels exceeded 0.3 ng/ml. If the AFP level ing) or streptavidin, each of which was conjugated with HRP, for 1hour at room temperature. After brief washing with TBS-T, 100 μl of a TMP substrate solution (Thermo Fisher Scientific) was added into each well, and the reactions were halted with 2N sulfuric acid. Then, the absorbance at 450 nm was measured.

1-11. Stability Test

Deglycosylated antibody was prepared by incubating 10 μg of a commercially available anti-hAFP antibody (#MIA1305, Thermo Fisher Scientific) with 100 units of PNGase-F (NEB) in Rapid PNGase-F (non-reducing format) buffer for 15 min at 50° C. Time- and temperature-dependent protein stability was measured by incubating glycosylated, deglycosylated, or aglycosylated antibodies in PBS buffer at either 4° C. or 37° C. for up to 14 days. The incubated antibodies were electrophoresed on 4 to 20% Mini-Protein TGX™ gels (Bio-Rad) and visualized by Coomassie blue staining. The protein stability was also monitored by incubating antibodies in 0.1M phosphate buffer adjusted to pH 3.0, 7.0, or 10.0 for 0 to 14 days.

Alternatively, each antibody was incubated in PBS buffer containing 0 to 3% $H_2O_2$ in an incubator at 37° C. for 5 hours. The integrity of the antibodies was measured by the ELISA assay described above.

1-12. Statistical Analysis

Statistical tests for indel efficiency were performed in Sigma Plot through a two-tailed Student's t test. P values<0.05 were considered significant.

EXAMPLE 2

Establishment of Aglycosylated Antibody-Producing Mice by Genome Editing

Immunoglobulins (IgGs) are N-linked glycoproteins that show heterogeneity in the glycan structure, as glycoproteins usually do. This molecular nature has restricted the use of routine immunoassays such as ELISA or CLIA in detecting disease-specific glycoprotein-biomarkers using glycan-specific probes including lectins. Meanwhile, lectins may be bound to the capture antibody even in the absence of an analyte (FIG. 1), and the glycan structure is difficult to predict and is subject to batch-to-batch variations, thereby producing uncontrollable, saturated blank values. This problem may be overcome by a specific glycoform assay through the immunoassay platform ALIQUAT (Aglycosylated antibody-Lectin coupled Immunoassay for the QUAntification of Tumor marker) using a suitable lectin and aglycosylated antibodies (FIG. 2). Thus, in this Example, mice that produce aglycosylated antibodies were established by genome editing.

2-1. Confirmation of Genome Editing in Mouse Zygotes

Several approaches have been developed to improve HDR efficiency, but it still remains significant low compared to non-homologous end-joining (NHEJ)-based knockout efficiency. Recently, base-editing systems have been developed in which 'C-G to T-A' and 'A-T to G-C' conversions can be made with no double-stranded DNA breakage, but rather with high efficiency by cytosine or adenine base editors. Sequence analysis of IgG genes of C57BL/6 mice revealed that IgG2b, IgG2c, and IgG3 share editable adenines at an N-glycosylation asparagine coding sequence (AAC) within a base editing window (FIG. 3). The conversion of either one or both of adenines to guanine creates non-asparagine-coding sequences, thereby eliminating N-glycan from IgGs.

Thus, in order to establish aglycosylated antibody-producing mice, according to Example 1-3, ABE7.10 mRNA and guide RNAs targeting IgG2b, IgG2c, and IgG3 were injected into zygotes of C57BL/6 mice to induce modification of the corresponding genes. Thereafter, genotyping was performed according to Example 1-4. Genotyping was performed for pups born (n=24) by the amplification refractory mutation system (ARMS), in which primers were designed to generate an additional PCR product of a different size when A to G conversion was made as indicated with an arrow (FIG. 4).

The assay results indicated that highly efficient A to G conversions were observed for all the IgG genes. The conversion rates (conversion of at least one locus) were 79.1% (19/24) for IgG2c, 87.5% (21/24) for IgG2b, and 62.5% (15/24) for IgG3. Comparison of the genotype screening results identified 15 pups that appeared to show simultaneous conversions at the three genes, nine of which were individually subjected to Sanger sequencing analysis. As a result, it was confirmed that all nine pups were identified to carry mutations at the three gene loci (IgG2c (FIG. 5), IgG2b (FIG. 6) and IgG3 (FIG. 7)) if chimeric mutations were included.

2-2. Establishment of Intermediate Founder Mice with Edited IgG2b, IgG2c and IgG3 Genes Among the nine pups screened in Example 2-1, one pup (#11) was selected for use in genome editing at the IgG1 locus, because it had higher biallelic "A to G" conversion rates in the IgG2c (FIG. 8), IgG2b (FIG. 9) and IgG3 (FIG. 10) genes than other pups. This pup showed a homozygous mutation at IgG2b and chimeric mutations at IgG2c and IgG3 (FIG. 11).

TABLE 6

| Gene | Edited target nucleotide sequence (5'→3') | SEQ ID NO |
|---|---|---|
| IgG2b | TACGACAGTACTCTCCGGGTGG | SEQ ID NO: 37 |
| IgG2c | TACGACAGTACTCTCCGGGTGG | SEQ ID NO: 38 |
| IgG3 | TACGACAGTACCTTCCGAGTGG | SEQ ID NO: 39 |

Pups generated by crossing of genome-edited pups and wild-type C57BL/6 mice were subjected to several rounds of crossing with heterozygous mutant pups and breeding so that the finally generated pups carried one of the mutant amino acid motifs, D-S-T, D-G-T, G-S-T, and G-G-T. A D-S-T mutant pup was selected as an intermediate founder for the following reasons: the N-glycosylation asparagine residue is located at the exposed loop between two strands of the immunoglobulin β-sandwich fold, and thus aspartic acid that exhibits an identical geometry to that of asparagine can avoid potential geometrical instability, unlike glycine (GST), even though it has a charged side chain. The introduction of two mutations such as D-G-T or G-S-T was excluded to minimize the modification of the structure (FIG. 12). This intermediate founder was bred and used for IgG1 gene editing.

2-3. Establishment of Founder Mice with Edited IgG1, IgG2b, IgG2c and IgG3 Genes The target site of IgG1 contains no canonical (NGG), but both strands of the target contain only the NG PAM sequence. Thus, HDR-mediated gene editing was performed using a donor DNA targeting a possible adjacent site, but a pup with an edited IgG1 gene could not be generated. Thus, for IgG1 gene editing, the IgG1 gene was edited according to Example 1-3 using the xCas9-ABE of Example 1-2 that exhibits gene targeting activity for an NG sequence.

As a result, heterogeneic conversion appeared in two pups, in which one allele was converted to a serine-encoding sequence (TCAGCAGCACTTTCCGTTCAGT; IgG1; SEQ ID NO: 40) (FIG. 13). The edited pup was subjected to several rounds of crossing and breeding until a homozygous IgG1 mutation was achieved. All the mutations showed a germline transmission and the founder with stacked aglycosylation mutations at IgG1, IgG2b, IgG2c, and IgG3 was successfully established. The mutations at the four alleles were again confirmed by Sanger sequencing. Detailed information on genome editing procedures is shown in Table 7 below.

TABLE 7

| Subclass | Method | Effector protein | Effector/ gRNA | Amino acid modification | Number of zygotes | | | Pups born | Mutants (monoallelic/ biallelic) |
|---|---|---|---|---|---|---|---|---|---|
| | | | | | Collected | Injected | Transferred | | |
| IgG1 | Adenine base editing | xCas9-ABE7.10 | mRNA/RNA | NST→SST | 211 | 196 | 32 | 10 | 7/0 |
| IgG2b | | ABE7.10 | | NST→DST | 405 | 317 | 112 | 24 | 10/11 |
| IgG2c | | | | | | | | | 12/7 |
| IgG3 | | | | | | | | | 5/10 |

EXAMPLE 3

Confirmation of Production of Aglycosylated Monoclonal Antibody against Human AFP in Genome-Edited Mice 3-1. Confirmation of Ability to Produce Every Subclass of Immunoglobulins The N-glycosylation of immunoglobulin G (IgG) is highly conserved among higher eukaryotic organisms, including mice, rabbits and humans. Although there are reports that IgG N-glycosylation confers stability or is involved in immune response regulation, whether higher organisms adopt N-glycosylation of IgG due to evolutionary pressure still remains unclear.

Thus, in order to examine whether defective IgG is produced, IgG profiling was performed using an immunoglobulin isotyping kit for the IgG derived from the genome-edited mice established in Example 2.

As a result, it was confirmed that the genome-edited mice displayed an identical profile to that of a wild-type mouse (FIG. 14), whereas mice with knockout of the IgG2b (FIG. 15) and IgG3 (FIG. 16) genes showed defects in the production of the corresponding subclasses.

This result confirmed that the genome-edited mice retain the ability to produce every subclass of immunoglobulins.

3-2. Confirmation of Aglycosylated Antibody Production

Whether antibodies produced form genome-edited mice are aglycosylated antibodies was examined.

Specifically, human AFP, which is one of the best-characterized tumor markers for hepatocellular carcinoma, was used as a model antigen. hAFP emulsified with an equal amount of adjuvants was injected into the hind footpads of 6-week-old genome-edited mice (n=5) five times at 1-week intervals. Sera were collected at each immunization step and used for direct ELISA analysis against hAFP.

As a result, it was confirmed that the reactivity increased over time (FIG. 17), indicating that immunizations occurred.

After completion of immunizations, popliteal lymph node cells were collected from the mice and fused with FO myeloma cells according to Example 1-5. Hybridoma cells were allowed to form colonies on hypoxanthine-aminopterin-thymidine (HAT)-containing plates, thus obtaining 666 hybridoma clones.

As a result, it was confirmed that, among the hybridoma clones, 93 clones (13.8%) secreted an antibody that was highly reactive to hAFP (FIG. 18).

3-3. Selection of Hybridoma Clones Having Excellent Monoclonal Antibody Productivity Since anti-hAFP antibodies may show cross-reactivity to epitopes present in human serum albumin (HSA), reactivity for HSA was checked and reactive clones were excluded. In addition, clones that showed decreased antibody productions over time were excluded, and three clones, which showed continuous antibody production, were selected and designated 1E5, 2A2, and 3A5, respectively. It was confirmed that the three clones all secreted a monoclonal antibody of the IgG1 subclass and kappa light chains (FIG. 19). In addition, MS analysis confirmed that there were no post-translational modifications in the mutated regions that were newly formed, such as O-linked glycosylation.

3-4. Confirmation of Aglycosylation of Antibodies Produced in Selected Hybridoma Clones To further confirm that the produced antibody is completely aglycosylated, lectin blot analysis using concanavalin A (Con-A) and immunoblot analysis using anti-mouse IgG antibodies were performed.

As a result, it was confirmed that, unlike a commercially purchased antibody that reacts with Con-A as indicated by an arrow, the heavy chains of the antibody (1E5) had no N-glycan (FIG. 20). Although IgGs allow the transfer of N-glycans to the outside of the CH2 region, it was confirmed that the three clones selected in Example 3-3 showed no trace of N-glycosylation (FIG. 21).

EXAMPLE 4

Feasibility Test for Aglycosylated Antibodies by Lectin-Coupled ELISA 4-1. Preparation of $FUT8^{-/-}$ Mutant Clones to Produce L3-Null AFP Standard HEK293-T cells express α-(1,6)-fucosyltransferase (FUT8), which catalyzes the transfer of GDP-fucose to the core N-glycan. There are three splicing variants for the FUT8 gene, and exons 9 and 11 belong to glycosyltransferase family 23, which is associated with catalytic activity and is shared by all the variants.

To establish an ALIQUAT (Aglycosylated antibody-Lectin coupled Immunoassay for the QUAntification of Tumor marker) system, exons 9 and 11 were separately targeted using CRISPR-Cas9 according to Example 1-7 to produce an L3-null AFP, because it is important to obtain an AFP-L3-deficient hAFP standard, before the feasibility of the produced aglycosylated antibody was tested in the sandwich ELISA platform according to Example 1-10.

As a result, each $FUT8^{-/-}$ mutant clone that showed a frame-shifted non-sense mutation was obtained (FIG. 22).

4-2. Examination of Whether $FUT8^{-/-}$ Cells Produce AFP-L3

To investigate functional loss by FUT8 gene ablation, lectin binding was tested according to Example 1-9 using a lectin derived from the mushroom Pholiota squarrosa (PhoSL) known to show a specific binding property for core-fucosylated N-glycans. Immunofluorescence analysis results indicated that $FUT8^{-/-}$ HEK293-T cells were resistant to PhoSL binding (FIG. 23).

Meanwhile, hAFP was overexpressed in both wild-type and FUT8$^{-/-}$ HEK293-T cells, and the conditioned media were collected for lectin-affinity electrophoresis. Electrophoresis of proteins was performed on agarose gels containing LCA, on which AFP-L3 and AFP-L1 show different mobility. The different glycoforms of AFP were visualized by immunoblotting using an anti-hAFP antibody (FIG. 24). It was confirmed that AFP-L3 comprised the majority of the AFP glycoforms obtained from wild-type HEK293-T cells, whereas FUT8$^{-/-}$ cells did not produce AFP-L3. In addition, mass analysis confirmed the absence of AFP-L3 form in FUT8$^{-/-}$ cells, and the percent AFP-L3 produced in the wild-type cells was 99.5% (FIG. 25). Similar results were also obtained in μ-Tas analysis.

4-3. Feasibility Test of Aglycosylated Antibodies in ALIQUAT System

A standard curve was produced by both canonical sandwich ELISA and AAL lectin-coupled ELISA.

Specifically, for the canonical sandwich ELISA, an aglycosylated antibody (1E5) or a commercial antibody was used as a capture antibody. A detection antibody pair was selected from commercially available antibodies, which are known to be a matched pair with the capture antibody. Analysis of the standard curve indicated that, although having a lower sensitivity than the validated commercial antibody, the aglycosylated antibody showed good linearity in the range of 0 to 20 ng/ml AFP (FIG. 26).

The feasibility of the aglycosylated antibody was demonstrated by AFP-L3 tests using AAL lectin (FIG. 27). Lectin ELISA using the commercial antibody showed considerable blank values, and increased concentrations of L3-positive AFP did not reflect a linear increase in the optical density, resulting in high standard errors. This pattern was similarly observed for both L3-positive and – negative AFP samples. However, the lectin-ELISA test using the aglycosylated antibody produced a standard curve with good linearity for L3-positive AFP samples. No interference was observed in the range of 0 to 1,000 ng/ml, and it was confirmed that the assay using a combination of a lectin and the aglycosylated antibody provides a valid analytical platform for the assay of specific glycoforms.

EXAMPLE 5

Confirmation of Possibility of Aglycosylated Antibody-Based Lectin-ELISA hAFP Test to Replace μ-TAS Analysis μ-TAS is an in vitro diagnostic immunoanalyzer that analyzes the electrophoretic mobility of AFP-L3 in a capillary tube including LCA. The high sensitivity and robustness of the analyzer and clinical utility of the AFP-L3 assay have allowed μ-TAS to gain FDA approval for the in vitro assessment of HCC development risk. Despite the analytical validity and clinical utility, μ-TAS analysis has several limitations in clinical use. That is, it is a high-cost assay, which has limited its routine clinical use for cancer screening. Moreover, μ-TAS has been developed for use in AFP-L3 tests, and is difficult to use in other glycoform analysis.

On the other hand, the ALIQUAT method can provides a versatile and universal platform for the detection of a wide range of disease-specific glycoforms. However, the ALIQUAT platform can be easily applied to the test of other disease-specific glycoforms only when a glycoform-specific probe and an aglycosylated antibody are available. Various lectins with specificity for tumor-specific biomarkers are already available. Thus, in order to confirm whether the aglycosylated antibody that can be easily produced from the genome-edited mouse of the present disclosure can be applied to the ALIQUAT method, the validity of the analysis was examined by applying clinical samples to a chemiluminescent immunoassay (CLIA) platform in which an aglycosylated antibody (1E5) is conjugated to a magnetic bead to detect hAFP in serum and a fucosylated form is traced by AAL.

Specifically, AFP-L3 standard molecules were spiked into a normal serum having an AFP level of less than 1 ng/ml. The standard curve showed good linearity in the range of 0 to 100 ng/ml (FIG. 28). Next, sera (n=19) were collected from normal volunteers and patients with hepatitis, cirrhosis and HCC. Serum showing AFP levels higher than 100 ng/mL was diluted so that the concentration was within the range of the standard curve. Each serum was split into equal volumes and measured through the ALIQUAT method and μ-TAS analysis according to Example 1-8.

The measured values were plotted as the AFP level on the X-axis and the percent AFP-L3 on the Y-axis. As a result of comparing the values obtained from the two platforms, it was confirmed that the comparative analysis showed p value>0.05, indicating that the two tests showed substantially the same results (FIG. 29).

EXAMPLE 6

Preserved Protein Stability of Aglycosylated Antibodies

Protein glycosylation is known to exhibit various effects such as protein function, protein-protein interaction, and host cell recognition. In addition, protein glycans are known to confer protein stability in vivo and in vitro (Bowden 2012). Thus, whether the antibodies lose protein stability by deglycosylation during storage and testing was examined according to Example 1-11.

Specifically, in order to investigate the stability of antibodies under various conditions, commercially available glycosylated antibodies and the deglycosylated antibody form produced by PNGase-F treatment were used as a control.

6-1. Examination of Thermal Stability of Protein

Different forms of antibodies were allowed to stand at 4° C. and 37° C. up to 14 days in PBS buffer. It was confirmed that the deglycosylated antibody showed two different degradation fragments as indicated with an arrow (FIG. 30). One of the fragments, with a molecular mass of about 35 kDa, was thought to arise from the PNGase-F treatment, because the fragment was observed from the early incubation time. A fragment with a molecular mass of about 50 kDa increased with time at 37° C. However, the original glycosylated form did not show any degradation products under the investigated conditions. Similarly, the present inventors could not detect any trace of degradation products for aglycosylated antibodies on the gels.

These results indicate that conditions for the deglycosylation reaction account for the loss of stability, rather than the absence of the glycan itself.

6-2. Examination of pH Stability of Protein

Antibodies may be exposed to changes in pH, according to various reaction conditions or during purification. Thus, the stabilities of the different glycoforms of antibodies under different pH conditions were examined.

Specifically, after the antibodies were incubated in buffers of pH 3.0, 7.0, and 10.0 at 37° C. for 14 days, the antibodies were used as a capture antibody in the measurements of hAFP. The optical density values in the test were measured and the protein's avidity was evaluated. As a result, it was found that the glycosylated and aglycosylated antibodies showed similar stabilities (FIG. 31). Both antibodies showed high stability for 14 days under neutral (pH 7.0) and high resistance under basic (pH 10.0) conditions, whereas their stability decreased in a time-dependent manner at pH 3.0. In contrast, the deglycosylated form showed a significant loss in integrity even in neutral pH. About 50% of the antibodies incubated at pH 7.0 for 14 days lost their avidity, and the loss was more prominent for incubations at pH 10.0. In particular, the deglycosylated form showed a complete loss of avidity after incubation at pH 3.0 for 4 days.

6-3. Examination of Protein Stability Under Oxidative Conditions

The integrity of antibodies was examined under oxidative conditions, and as a result, it was confirmed that both glycosylated and aglycosylated antibodies showed resistance against such conditions, which was in significant contrast to the physical properties of the deglycosylated form (FIG. 32). The aglycosylated antibody showed a stability loss of less than 10% when incubated in PBS buffer containing 3.0% $H_2O_2$ for 1 hour. However, it was confirmed that a deglycosylated antibody lost about 50% of its avidity under these conditions. From these results, it was confirmed that the stability of aglycosylated antibodies did not become lower than that of glycosylated immunoglobulin G.

So far, the present disclosure has been described with reference to the embodiments. Those of ordinary skill in the art to which the present disclosure pertains will appreciate that the present disclosure may be embodied in modified forms without departing from the essential characteristics of the present disclosure. Therefore, the disclosed embodiments should be considered from an illustrative point of view, not from a restrictive point of view. The scope of the present disclosure is defined by the claims rather than the foregoing description, and all differences within the scope equivalent thereto should be construed as being included in the present disclosure.

---

The invention claimed is:

1. An aglycosylated antibody-producing animal model obtained by modification of immunoglobulin G (IgG) gene, wherein the modification comprises at least one substitution selected from the group consisting of:
   substitution of a sequence corresponding to SEQ ID NO: 2 with the sequence of SEQ ID NO: 40;
   substitution of a sequence corresponding to SEQ ID NO: 3 with the sequence of SEQ ID NO: 37;
   substitution of a sequence corresponding to SEQ ID NO: 4 with the sequence of SEQ ID NO: 38; and
   substitution of a sequence corresponding to SEQ ID NO: 5 with the sequence of SEQ ID NO: 39.

2. The aglycosylated antibody-producing animal model of claim 1, wherein the animal is a rabbit, a goat or a mouse.

3. A method for producing an aglycosylated antibody against an antigen, the method comprising administering the antigen to be detected to the animal model of claim 1, and
   producing an aglycosylated antibody in the animal.

4. An aglycosylated antibody produced by the method of claim 3.

5. An immunoassay kit comprising:
   the aglycosylated antibody of claim 4; and
   a glycoprotein biomarker.

6. The immunoassay kit of claim 5, wherein the glycoprotein biomarker is detected by lectin.

7. The immunoassay kit of claim 6, wherein the lectin is capable of specifically detecting the glycoprotein biomarker.

8. The immunoassay kit of claim 5, wherein the glycoprotein is alpha-fetoprotein (AFP)-L3.

* * * * *